(12) United States Patent
Turner

(10) Patent No.: US 7,476,504 B2
(45) Date of Patent: Jan. 13, 2009

(54) USE OF REVERSIBLE EXTENSION TERMINATOR IN NUCLEIC ACID SEQUENCING

(75) Inventor: Stephen Turner, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 365 days.

(21) Appl. No.: 11/341,041

(22) Filed: Jan. 27, 2006

(65) Prior Publication Data

US 2006/0183145 A1 Aug. 17, 2006

Related U.S. Application Data

(60) Provisional application No. 60/649,009, filed on Jan. 31, 2005.

(51) Int. Cl.
*C12Q 1/68* (2006.01)
*C12M 1/00* (2006.01)

(52) U.S. Cl. .................. 435/6; 435/91.1; 435/287.2

(58) Field of Classification Search ............... None
See application file for complete search history.

(56) References Cited

U.S. PATENT DOCUMENTS

| | | | |
|---|---|---|---|
| 5,143,854 A | 9/1992 | Pirrung et al. | |
| 5,302,509 A | 4/1994 | Cheeseman | |
| 5,412,087 A | 5/1995 | McGall et al. | |
| 5,773,308 A | 6/1998 | Conrad et al. | |
| 6,087,095 A | 7/2000 | Rosenthal et al. | |
| 6,399,335 B1 | 6/2002 | Kao et al. | |
| 2003/0175780 A1 | 9/2003 | Jones | |
| 2003/0215862 A1* | 11/2003 | Parce et al. ............. | 435/6 |
| 2006/0060766 A1* | 3/2006 | Turner et al. ........... | 250/251 |

OTHER PUBLICATIONS

Burgess, Kevin, et al. 1997. Photolytic Mass Laddering for Fast Characterization of Oligomers on Single Resin Beads. *J. Org. Chem.* 62(17); 5662-5663.
De Luca, Lidia, et al. 2001. A New Supported for the Photochemical Generation of Radicals in Solution. *Org. Lett.* 3(6): 855-857.
Fang, Shiyue, et al. 2003. Reversible Biotinylation Phosphoramidite for 5'-End-Labeling, Phosphorylation, and Affinity Purification of Synthetic Oligonucleotides. *Bioconjugate Chem.* 14(1); 80-85.
Glatthar, Ralf, et al. 2000. A New Photocleavable Linker in Solid-Phase Chemistry for Ether Cleavage. *Org. Lett.* 2(15): 2315-2317.
Goldmacher, Victor S., et al. 1992. Photoactivation of Toxin Conjugates. *Bioconjugate Chem.* 3(2): 104-107.
Guillier, Fabrice, et al. 2000. Linkers and Cleavage Strategies in Solid-Phase Organic Synthesis and Combinatorial Chemistry. *Chem. Rev.* 100(6): 2091-2157.
Holmes, Christopher P. 1997. Model Studies for New o-Nitrobenzyl Photolabile Linkers: Substituent Effects on the Rates of Photochemical Cleavage *J. Org. Chem.* 62(8); 2370-2380.
Hu, Jun, et al. 2001. Competitive Photochemical Reactivity in a Self-Assembled Monolayer on a Colloidal Gold Cluster. *J. Am. Chem. Soc.* 123(7): 1464-1470.
Kessler, Martin, et al. 2003. Sequentially Photocleavable Protecting Groups in Solid-Phase Synthesis. *Org. Lett.*5(8); 1179-1181.
Kim, Hanyoung, et al. 2004. Core-Shell-Type Resins for Solid-Phase Peptide Synthesis: Comparison with Gel-Type Resins in Solid-Phase Photolytic Cleavage Reaction. *Org. Lett.* 6(19): 3273-3276.
Maxam, Allan M., et al. 1977. A new method for sequencing DNA. *Proc. Natl. Acad. Sci. U.S.A.* 74(2): 560-564.
Nadji, Sourena, et al. 1992. Photochemically and photoenzymatically cleavable DNA. *J. Am. Chem. Soc.*114(24):9266-9269.
Nielsen, Peter E., et al. 1991. Photolytic cleavage of DNA by nitrobenzamido ligands linked to 9-aminoacridines gives DNA polymerase substrates in a wavelength-dependent reaction. *Bioconjugate Chem.* 2(1): 57-66.
Orain, David, et al. 2002. Protecting Groups in Solid-Phase Organic Synthesis. *J. Comb. Chem.* 4(1): 1-16.
Ottl, Johannes, et al. 1998. Preparation and Photoactivation of Caged Fluorophores and Caged Proteins Using a New Class of Heterobifunctional, Photocleavable Cross-Linking Reagents. *Bioconjugate Chem.* 9(2); 143-151.
*PCR 2: A Practical Aproach.* (M.J. McPherson, B.D. Hames and G.R. Taylor eds., 1995) Table of Contents only, pp. ix-xvii.
Pellois, Jean-Philippe, et al. 2004. Simultaneous Triggering of Protein Activity and Fluorescence.*J. Am. Chem. Soc.(Communications).* 126(23): 7170-7171.
Quirk, Michael and Julian Serda. 2001. *Semiconductor Manufacturing Technology.*Upper Saddle River: Prentice Hall. Table of Contents only, pp. iii-x.

(Continued)

*Primary Examiner*—James Martinell
(74) *Attorney, Agent, or Firm*—Wilson Sonsini Goodrich & Rosati

(57) ABSTRACT

The present invention relates to the uses of reversible extension terminator in conjunction with optical confinements in nucleic acid sequencing. The apparatus and methods embodied in the present invention are particularly useful for high-throughput and low-cost nucleic acid sequencing.

51 Claims, 9 Drawing Sheets

OTHER PUBLICATIONS

Roskey, Mark T., et al. 1996. DNA sequencing by delayed extraction-matrix-assisted laser desorption/ionization time of flight mass spectrometry. *Proc. Nat'l. Acad. Sci. USA*. 93: 4724-4729.

Sambrook, J. et al. 1989. *Molecular Cloning: A Laboratory Manual. 2nd Edition*. New York: Cold Spring Harbor Laboratory Press. Table of Contents only, pp. v-xxxii.

Sanger, F., et al. 1977. DNA sequencing with chain-terminating inhibitors. *Proc. Natl. Acad. Sci U.S.A.* 74(12): 5463-5467.

Sauer, M., et al. 1999. Detection and Identification of Single Dye Labeled Mononucleotide Molecules Released from an Optical Fiber in a Microcapillary: First Steps Toward a New Single Molecule DNA Sequencing Technique, *Phys. Chem Chem. Phys*.1: 2471-77.

Seo, Taek Seok, et al. 2005. Four-color DNA sequencing by sythesis on a chip using ph fluorescent nucleotides. *Proc. Natl. Acad. Sci. U.S.A.* 102(17); 5926-5931.

Soughayer, Joseph S., et al. 2004. Characterization of TAT-Mediated Transport of Detachable Kinase Substrates. *Biochemistry.* 43(26); 8528-8540.

Tang, XinJing, et al. 2005. Phototriggering of Caged Fluorescent Oligodeoxynucleotides. *Org. Lett.* 7(2); 279-282.

Wolf, Stanley. 1995. *Silicon Processing for the VLSI Era*. Sunset Beach: Lattice Press. Table of Contents only, pp. v-xx.

Yan, Funing, et al. 2004. Synthesis and Characterization of a Photocleavable Cross-Linker and Its Application on Tunable Surface Modification and Protein Photodelivery. *Bioconjugate Chem.* 15(5): 1030-1036.

Levene, et al. Zero-Mode Waveguides for Single-Molecule Analysis at High Concentrations. *Science*. 2003; 299:682-686.

* cited by examiner a.) Example of a photocleavable blocker:
1-(aminomethyl-2-nitrophenyl) ethyl carbonate cleavage occurs around 340 nm b.)

cleavage wavelength 350 nm c.)

d.)

1-(2-nitrophenyl) ethyl 1-(2-nitro-4-methylamino phenyl) ethyl cleavage occurs around 340 - 350 nm

USE OF REVERSIBLE EXTENSION TERMINATOR IN NUCLEIC ACID SEQUENCING

CROSS REFERENCE TO RELATED APPLICATIONS

This application claims priority to Provisional U.S. Patent Application No. 60/649,009, filed Jan. 31, 2005, the full disclosure of which is incorporated herein by reference in its entirety for all purposes.

TECHNICAL FIELD

The present invention relates to the uses of reversible extension terminator in conjunction with optical confinements in nucleic acid sequencing. The apparatus and methods embodied in the present invention are particularly useful for high-throughput and low-cost nucleic acid sequencing.

BACKGROUND OF THE INVENTION

The advent of DNA sequencing technology has revolutionized molecular biology through vastly extending the capability to identify and delineate DNA compositions from any biological sources. Nowadays, DNA sequencing is routinely employed in the course of conducting scientific research, and it is becoming more commonly practiced in clinical diagnostics, environmental studies, and forensic investigations.

Sanger's dideoxy termination method (Sanger et al., Proc. Natl. Acad. Sci. U.S.A. 74: 563-5467 (1977)) and Maxam-Gilbert's chemical degradation method (Maxam and Gilbert, Proc. Natl. Acad. Sci. U.S.A. 74: 560-564 (1977)) are the two traditional procedures commonly practiced in the field. Both methods require four samples with each sample containing a family of DNA strands in which all strands terminate in the same nucleotide. Upon termination of the polymerization reactions, gel electrophoresis, or more recently capillary array electrophoresis is used to resolve the different length strands terminated at different base positions and to determine the nucleotide sequence, either by differentially tagging the strands of each sample before electrophoresis to indicate the terminal nucleotide, or by running the samples in different lanes of the gel or in different capillaries. These procedures are labor- and time-intensive. Improved DNA sequencing techniques that overcome the limitations of electrophoresis have been developed. Such techniques include pyrosequencing, MS sequencing (Fu, D. J. et al. (1998) National Biotechnol. 16, 381-384; Roskey, M. T. et al. (1996) Proc. Natl. Acad. Sci. USA 93, 4724-4729; J. R., Itagaki et al. (2001) Nucleic Acids Res. 29, e104), sequencing by hybridization (Drmanac, S. et al. (1998) Nat. Biotechnol. 16, 54-5810), sequence-specific detection of single-stranded DNA using engineered nanopores.

More recently, new DNA sequencing approaches based on a solid surface have been reported. One example of this approach involves the use of nucleotides or nucleotide analogues known as chain or extension terminators. These extension terminators prevent further addition by the polymerase of nucleotides or nucleotide analogs to the 3' end of the nascent DNA strand once they are incorporated into the nascent strand. In practice, in order to obtain consecutive base sequences of a template DNA, the extension terminators must be washed off before the next round of base incorporation event can take place. See, for example, U.S. Pat. Nos. 5,302, 509 and 6,087,095. The requisite washing step between each base incorporation event is thus the rate-limiting step, which inevitably delays the sequencing process. Furthermore, the washing step causes the displacement of costly reagents in the reaction including polymerases and nucleotide analogs.

Thus, there remains a considerable need for alternative methods and devices designed to perform high-throughput and cost-effective nucleic acid sequencing.

SUMMARY OF THE INVENTION

The present invention relates to uses of reversible extension terminator in conjunction with optical confinements in nucleic acid sequencing. The subject methods eliminate the need for the step of washing, and take advantage of the deferral of detection associated with reversible extension terminators.

Accordingly, the present invention provides a method for identifying a base in a template nucleic acid. The method comprises the steps of (a) providing an optical confinement; (b) providing a reaction mixture within the optical confinement, the reaction mixture comprising the template nucleic acid, a polymerase enzyme, and at least a first nucleotide analog, wherein the first nucleotide analog comprises a removable blocking group that terminates chain extension of a nascent nucleic acid strand when the first nucleotide analog is incorporated into the nascent nucleic acid strand; and (c) identifying the base in the template nucleic acid strand by detecting the incorporated nucleotide analog. The method may further comprise the step of removing the removable blocking group; and repeating the providing and identifying steps of (b) and (c) with at least a second nucleotide analog that comprises a removable blocking group that terminates chain extension of a nascent nucleic acid strand when the second nucleotide analog is incorporated into the nascent nucleic acid strand. In some embodiments, the first nucleotide analog is present in the reaction mixture at a concentration greater than about 1 micromolar, greater than about 50 micromolar, or greater than about 100 micromolar. In general, the nucleotide analogs used in the present invention comprise detectable labels, such as fluorescent labels. In some embodiments, the first and second nucleotide analogs are concurrently present in the reaction mixture, each of which may comprise a fluorescent label, preferably distinct for each type of nucleotide analogs. In other embodiments, a single complex of the template nucleic acid and the polymerase enzyme is contained in the optical confinement described herein.

The aforementioned method can further comprise providing a plurality of optical confinements, providing a reaction mixture within each of the plurality of optical confinements, each reaction mixture comprising the template nucleic acid, a polymerase enzyme, and at least a first nucleotide analog, wherein the first nucleotide analog comprises a removable blocking group that terminates chain extension of a nascent nucleic acid strand when the first nucleotide analog is incorporated into the nascent nucleic acid strand. In one embodiment, the identifying step comprises detecting incorporation of the at least first nucleotide analog into a nascent nucleic acid strand in one or more of the plurality of optical confinements. In another embodiment, the identifying step comprises detecting incorporation in a subset of the plurality of optical confinements at a time. In yet another embodiment, the identifying step comprises detecting incorporation in one optical confinement at a time. In still yet another embodiment, the identifying step comprises monitoring a plurality of optical confinements at a time.

The present invention further provides a method for identifying a base in a template nucleic acid. The method involves the steps of (a) providing a reaction mixture comprising the template nucleic acid, a polymerase enzyme, and at least a first nucleotide analog, wherein the first nucleotide analog comprises a removable blocking group that terminates chain extension of a nascent nucleic acid strand when the first nucleotide analog is incorporated into the nascent nucleic acid strand; (b) identifying the base in the template nucleic acid strand by detecting the incorporated nucleotide analog; (c) removing the removable blocking group from the incorporated nucleotide analog; and (d) repeating at least the identifying and removing steps with at least a second nucleotide analog without depleting at least one reagent from the reaction mixture of (a). Where desired, the reaction mixture is provided in an optical confinement available in the art or in an optical confinement described herein.

The present invention also includes a method for conducting nucleic acid sequencing. The method generally involves (a) providing an optical confinement of the present invention; (b) mixing in the confinement the target nucleic acid molecules, primers complementary to the target nucleic acid molecules, polymerization enzymes, and more than one type of nucleotides or nucleotide analogs that are extension terminators to be incorporated into nascent nucleotide strand; (c) subjecting the mixture to a polymerization reaction under conditions suitable for formation of the nascent nucleotide strand by template-directed extension of primer; (d) illuminating the optical confinement with an incident light beam to cleave the blocking group on the terminator and/or to identify the nucleotide that is incorporated into the nascent nucleotide strand of at least two consecutive bases.

Any other variations described herein with respect to the choice of nucleotide analogs, blocking groups, concentrations thereof, detecting means or systems are applicable for any methods of the present invention.

The present invention also provides a system, comprising: an optical confinement; a reaction mixture disposed within the optical confinement, the reaction mixture comprising a template nucleic acid, a polymerase enzyme, and at least a first nucleotide analog, wherein the first nucleotide analog comprises a removable blocking group that terminates chain extension of a nascent nucleic acid strand when the first nucleotide analog is incorporated into the nascent nucleic acid strand. In some embodiments, the detector positioned proximal to the optical confinement to detect incorporation of the first nucleotide analog into the nascent nucleic acid strand. In other embodiments, the first nucleotide analog comprises a fluorescent label, and the detector comprises a fluorescence detector. In other embodiments, the optical confinement comprises a zero mode waveguide disposed upon or within a substrate. In some other embodiments, a single complex of the template nucleic acid and the polymerase enzyme is contained in the optical confinement of the present system.

The present invention also provides optical confinements suitable for performing the methods described herein including but not limited to conducting sequencing with the use of reversible extension terminators. In one embodiment, the present invention provides high density optical confinements, including those having a surface density exceeding $4 \times 10^4$ or $5 \times 10^5$ confinements per $mm^2$, wherein an individual confinement in the array provides an effective observation volume that is less than one nanoliters ($10X^{-9}$ liters), preferably on the order of zeptoliters. In certain aspects, each of the individual confinement provides an effective observation volume that is less than 100 zeptoliters, or less than 50 zeptoliters, or even less than 10 zeptoliters. In other aspects, each of the individual confinement yields an effective observation volume that permits resolution of individual molecules present at a concentration that is higher than one nanomolar, or higher than 100 nanomolar, or on the order of micromolar range. In certain preferred aspects, each of the individual confinement yields an effective observation volume that permits resolution of individual molecules present at a physiologically relevant concentration, e.g., at a concentration higher than about 1 micromolar, or higher than 50 micromolar range or even higher than 100 micromolar. The array may comprise zero-mode waveguides or other nanoscale optical structures that achieve the foregoing optical confinement.

Additional optical confinements suited for practicing the subject methods include field enhancement by sharp metal tips, nanotube confinement, thin slit confinement, near-field resonant energy transfer confinement, near field aperture confinement, diffraction limited optical confinement, stimulated emission depletion confinement, and as well as all other confinements described, for example, in co-pending U.S. Ser. No. 10/944,106, which is incorporated herein in its entirety for all purposes.

The array of optical confinements may further comprise another array of confinements that does not yield the above-described effective observation volume or does not permit resolution of individual molecules. For example, the array of optical confinements can be coupled to a microtiter plate that has a comparable surface density.

DETAILED DESCRIPTION OF THE INVENTION

Figure 1:
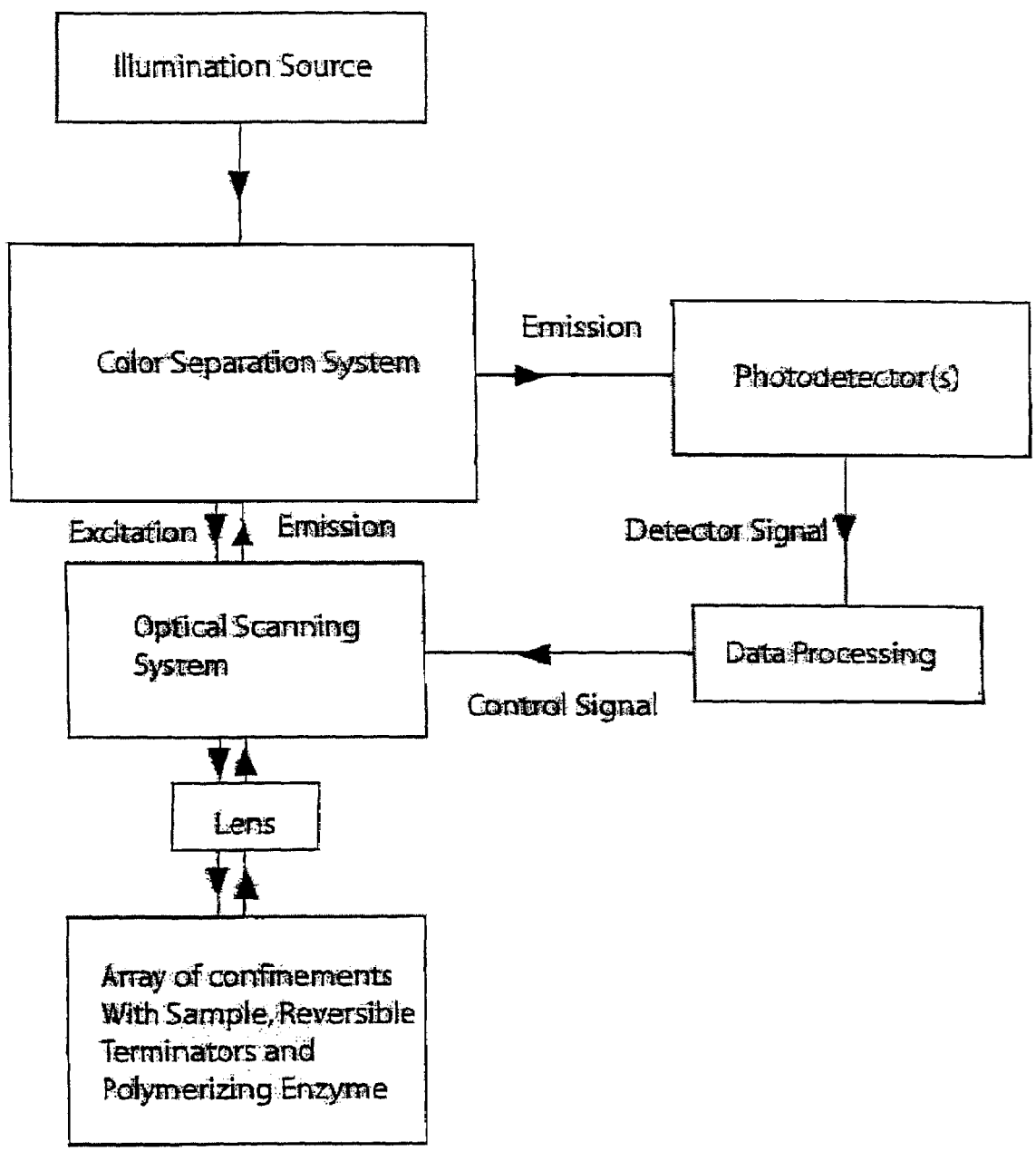
FIG. 1 is a schematic representation of the system applicable for performing nucleic acid sequencing according to the methods of the present invention.

General Techniques:

The practice of the present invention will employ, unless otherwise indicated, conventional techniques of Integrated Circuit (IC) processing biochemistry, chemistry, molecular biology, genomics and recombinant DNA, which are within the skill of the art. See, e.g., Stanley Wolf et al., SILICON PROCESSING FOR THE VLSI ERA, Vols 1-4 (Lattice Press); Michael Quirk et al., SEMICONDUCTOR MANU- FACTURING TECHNOLOGY; Sambrook, Fritsch and Maniatis, MOLECULAR CLONING: A LABORATORY MANUAL, $2^{nd}$ edition (1989); the series METHODS IN ENZYMOLOGY (Academic Press, Inc.): PCR 2: A PRACTICAL APPROACH (M. J. MacPherson, B. D. Hames and G. R. Taylor eds. (1995).

A "primer" is a short polynucleotide, generally with a free 3' OH group, that binds to a target or "template" potentially present in a sample of interest by hybridizing with the target, and thereafter promoting polymerization of a polynucleotide complementary to the target.

The term "hybridize" as applied to a polynucleotide refers to the ability of the polynucleotide to form a complex that is stabilized via hydrogen bonding between the bases of the nucleotide residues in a hybridization reaction. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. The hybridization reaction may constitute a step in a more extensive process, such as the initiation of a PCR reaction, or the enzymatic cleavage of a polynucleotide by a ribozyme.

Hybridization can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single stranded polynucleotides, the reaction is called "annealing" and those polynucleotides are described as "complementary". A double stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base pairing rules.

The present invention relates to uses of reversible extension terminator in conjunction with optical confinements in nucleic acid sequencing. The subject methods eliminate the need for the step of washing, and take advantage of the deferral of detection associated with reversible extension terminators. Deferral of detection is valuable because it allows the multiplexing of detectors (even in case of detectors with low-bandwidth) for monitoring many base incorporation events without creating the risk of missing the consecutive incorporation events when the detector's attention is directed elsewhere. While the detector technologies known in the art such as photomultiplier tubes and avalanche photodiodes can have very high bandwidth (e.g. 400 MHz for APD detector) and may cope with the speed of polymerases, which may exceed 1000 bases per second, it can still be advantageous to perform a wash-free sequencing involving reversible chain terminators for ease of multiplexed detection of the base incorporation events. In cases where there is no deferral of detection, several limitations may exist on the degree of multiplex that can result with a single detector channel. These limitations may stem from duty cycle considerations and/or shot noise considerations.

With respect to duty cycle, in order to multiplex, the detector may spend time away from any given channel while it collects light from the other channels. In a system that does not involve deferred detection, incorporation events to be observed have a strong random component in both their starting times and their durations. Because of this, any time spent away from a particular channel creates the possibility that an event could occur when the detector is not monitoring that channel, leading to a missed event and an error in the corresponding sequence determination. This can be ameliorated by switching channels on a timescale very fast compared with the average duration of an incorporation event (the time during which the molecular label is detectable). However, optical switching systems have practical limitations in some cases, and thus may pose a limit to the multiplex factor.

With regard to shot noise limitations, typically in single-molecule detection systems, one of the primary sources of noise is the photon shot noise associated with the small numbers of photons that are detected corresponding to each molecule. Irrespective of how fast the channels are switched, the total number of photons that can be detected in a multiplex system is reduced by a factor of 1/N, where N is the multiplex factor. Though photon emission rates can be increased by applying more intense illumination, there is a saturation limit to the number of photons per second that cannot be exceeded. Additionally, increases in illumination intensity generally increase the rate of photobleaching, which further decreases the amount of time available to the detector to accumulate photon counts.

One aspect of the present invention is the design of optical devices and methods for conducting nucleic acid sequencing. Distinguished from the previously reported nanostructures, the optical devices of the present invention allow multiplexing a massive quantity of single-molecule analyses under physiologically relevant conditions.

Accordingly, in one embodiment, the present invention provides a high density array of optical confinements having a surface density exceeding $4\times10^4$ confinements per $mm^2$, wherein the individual confinement in the array provides an effective observation volume on the order of zeptoliters. Preferably, the individual confinement in the array provides an effective observation volume less than about 1000 zeptoliters, more preferably less than about 900, more preferably less than about 80, even more preferably less than about 10 zeptoliter. Where desired, an effective observation volume less than 1 zeptoliter can be provided. In a preferred aspect, the individual confinement yields an effective observation volume that permits resolution of individual molecules present at a physiologically relevant concentration. The physiologically relevant concentrations for most biochemical reactions range from the micro-molar to millimolar because most enzymes have their Michaelis constants in these ranges. Accordingly, preferred arrays of optical confinements typically have an effective observation volume for detecting individual molecules present at a concentration higher than about 1 micromolar (uM), or more preferably higher than 50 uM, or even higher than 100 uM.

To achieve the required observation volume for single-molecule analyses under physiologically relevant conditions, the subject array generally comprises zero-mode waveguides or alternative nanoscale optical structures. Such alternative structures include but are not limited to porous films with reflective index media, and confinement using index matching solids. For example, using the methods of the present invention, one can detect numerous incorporation events, individually followed by removal of the chain terminating group, without substantially removing the other unincorporated reagents from the reaction mixture in time-consuming wash steps. Instead, the signal contributions from such reagents are screened through the use of optical confinements or other methods described elsewhere herein.

As used herein, "zero-mode waveguide" refers to an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such a guide provides an extremely small observation volume effective to detect single-molecules, even when they are present at a concentration as high as in the micromolar range.

The zero-mode waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation. Suitable materials for fabricating the cladding include but not limited to alloys, metals, and semi-conducting materials, and any combination thereof. Alloys include any of the numerous substances having metallic properties but comprising two or more elements of which at least one is a metal. Alloys may vary in the content or the amount of the respective elements-whether metallic or non-metallic. Preferred alloys generally improve some desirable characteristic of the material over a pure elemental material. Characteristics that can be improved through the use of mixtures of materials include, chemical resistance, thermal conductivity, electrical conductivity, reflectivity, grain size, coefficient of thermal expansion, brittleness, temperature tolerance, conductivity, and/or reduce grain size of the cladding.

In general, alloys suitable for the present invention may involve mixtures where one component is present at fractions as low as 0.0001%. In other instances, alloys with large fractions of more than one compound will be desirable. One embodiment of the ZMW uses aluminum as the cladding of the ZMW structure. As an example of how alloys can be beneficial to a ZMW structure, it is useful to consider different alloys of aluminum in how they would affect a ZMW. In the art of Metallurgy, numerous materials are alloyed with aluminum. Non-limiting examples of materials suitable to alloy with aluminum are antimony, arsenic, beryllium, bismuth, boron, cadmium, calcium, carbon, cerium, chromium, cobalt, copper, gallium, hydrogen, indium, iron, lead, lithium, magnesium, manganese, mercury, molybdenum, nickel, niobium, phosphorous, silicon, vanadium, zinc and others. By way of example of how the introduction of another element could beneficially impact the ZMW performance, the introduction of boron to aluminum is known in the art of metallurgy to increase the conductivity of aluminum. An increase in conductivity of the metal film could improve the performance by decreasing the penetration depth thereby decreasing the observation volume. A preferred embodiment includes an alloy of aluminum that is more than 0.0001% of a dopant. A more preferred embodiment includes an alloy of aluminum that is more than 0.005% of a dopant. A still more preferred embodiment includes an alloy of aluminum that is more than 0.1% of a dopant.

In contrast, some materials are expected to decrease the performance of the ZMW structure, and in these instances it will be desirable to take measures to eliminate certain impurities. For example, in certain applications it may be desirable to decrease the amount of lead or arsenic if toxicity of the device is a concern. A preferred embodiment of the device includes a metal film that is less than 1% arsenic. A more preferred embodiment of the device includes a metal films that is less than 0.1% arsenic. A still more preferred embodiment includes a metal film that is less than 0.001% arsenic. A still more preferred embodiment includes a metal film that is less than 0.00001% arsenic. An additional preferred embodiment includes a metal film that is less than 1% lead. A still more preferred embodiment includes a metal film that is less than 0.1% lead. A still more preferred embodiment includes a metal film that is less than 0.01% lead. A still more preferred embodiment includes a metal film that is less than 0.001% lead. A still more preferred embodiment includes a film that is less than 0.00001% lead. In other applications where optical confinement performance is especially important, impurities that tend to reduce the conductivity, thereby worsening the confinement, will be undesirable. For example, vanadium is known in the art of metallurgy to reduce the conductivity of aluminum. A preferred embodiment includes a metal film that is less than 0.1% vanadium. A still more preferred embodiment includes a metal film that is less than 0.01% vanadium. A still more preferred embodiment includes a film that is less than 0.001% vanadium.

Semi-conducting materials suitable for fabricating the cladding are generally opaque, and they include silicon, silicates, silicon nitride, gallium phosphide, gallium arsenide, or any combinations thereof.

The cladding of the subject zero-mode waveguide may be coated with materials to improve the surface quality. For instance, coating may enhance the durability of the cladding material. In addition, coating is particularly desirable if the reactants contained in the core are prone to interact or adhere to the cladding material. A variety of appropriate coating materials are available in the art. Some of the materials may covalently adhere to the surface, others may attach to the surface via non-covalent interactions. Non-limiting examples of coating materials include aluminum oxide film, silanization reagent such as dimethychlorosilane, dimethydichlorosilane, hexamethyldisilazane or trimethylchlorosilane, polymaleimide, and siliconizing reagents such as silicon oxide, Aquasil™, and Surfasil™.

In certain embodiments, it may be advantageous to construct the confinement from metal compositions that are inhomogeneous combinations of more than one material. For example, for certain applications, it may be beneficial to provide a composition that comprises more than one layer, each layer having a different composition, or composition that varies within a layer. This can have beneficial effects on several aspects of the performance of the confinement, including but not limited to the nature of the optical confinement, the structural strength and behavior of the device, the characteristics of the surface chemistry of the device or the like. In one embodiment the confinement comprises two layers in which one of the layers serves to enhance the adhesion of the second layer to a substrate. In another embodiment, the composition of the cladding film varies as a function of the axial position relative to the confinement, so as to provide different optical performance than would be obtained from a layer of uniform composition. In a particular version of this embodiment, the film comprises a composition that has a larger value of skin depth close to the surface of the substrate, and comprises a composition that has a smaller value of skin depth farther from the surface of the substrate, so that the nature of the confinement is to be more uniform in shape near the surface and then tapering off more quickly a larger distances away from the substrate. In another embodiment, the thicknesses of two different layers comprising the cladding of the confinement are chosen so that a specific optical condition is achieved at the substrate of the device, such as constructive or destructive interference.

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda_c$). For a circular guide of diameter d and having a clad of perfect conductor, $\lambda_c$ is approximately 1.7×d. The cross sectional area of the core may be circular, elliptical, oval, conical, rectangular, triangular, polyhedral, or in any other shape. The various shapes can have particular suitability for certain applications. For instance, elongated cross-sections can be useful to provide enhanced access to molecules with mechanical persistence or stiffness, such as DNA. Cross sections ranging from extended slots to ovals of various aspect ratio will significant increase the accessibility of the persistent molecule to the detection zone of the structure, without excessive compromise in the axial attenuation of radiation. Although uniform cross sectional area is preferred, the cross sectional area may vary at any given depth of the guide if desired.

In a preferred embodiment, the core is non-cylindrical. In one aspect of this embodiment, a non-cylindrical core comprises an opening on the upper surface and a base at the bottom surface that is entirely surrounded by the cladding, wherein the opening is narrower in lateral dimension than the base. This configuration significantly restricts the diffusion of reactants, and hence increases the average residence time in the observation volume. Such configuration is particularly useful for measuring the association rate constant (on-rate) of a chemical reaction. In another aspect, the core comprises an opening that is wider in lateral dimension than the base. Such configuration allows easier access to large molecules that impose a steric or entropic hindrance to entering the structure if the open end of the zero mode waveguide was as small as the base needed to be for optical performance reasons. Examples include the accessibility for long strand polyelectrolytes such as DNA molecules that are subject to entropic forces opposing entry into small openings.

The zero-mode waveguides embodied in the present invention have a relatively high fill fraction ratio, typically above 0.0001, preferably above 0.001, more preferably above 0.01, and even more preferably above 0.1. As used herein, "fill fraction" of a pattern refers to the ratio of the total area occupied by the pattern (foreground and background, together). In the context of zero-mode waveguide, the foreground is considered to be the area occupied by the core of the zero-mode waveguide, and the background is the area between the zero-mode waveguide (e.g., the aluminum film that forms the cladding in certain designs). The zero-mode waveguides with high fill fraction ratios are particularly useful for performing homogenous assays. The fill fraction can be calculated by summing the total areas of all of the zero-mode waveguides in the array and dividing by the total available area including both the zero-mode waveguides and the spaces between them.

The cutoff wavelength is the wavelength above which the waveguide is essentially incapable of propagating electromagnetic energy along the waveguide under the illumination geometry used. Given the geometry of the core, and the properties of the cladding material, as well as the wavelength of the incident electromagnetic radiation, one skilled in the art can readily derive the cutoff wavelength by solving the Maxwell's equations (see, e.g., John D. Jackson, CLASSICAL ELECTRODYNAMICS, second edition, John Willey and Sons). The choice of the incident wavelength will depend on the particular application in which the subject array is to be employed. In certain aspects, the incident wavelength may be selected from a range of about 10 m to about 1 mm. For detecting fluorescent signals, the incident wavelength is typically selected from the range of about 380 nm to about 800 nm. Polarized (linearly or preferably circularly polarized) or unpolarized incident radiation is generally employed to illuminate the array in order to create a desired observation volume.

In a separate embodiment, the present invention provides an alternative optical confinement termed external reflection confinement (ERC). In contrast to the conventional total internal reflection confinement (IRC), the low index medium is the electromagnetic radiation carrier, and the high index (and opaque) medium is the reflector. As such, the roles of the refractive indices are reversed as compared to the IRC situation. ERC generally requires some kind of means to provide the analyte (i.e., the molecules under investigation) in the opaque phase.

IRC relies on reflection of an electromagnetic radiation incident on an interface between high index of refraction and low index of refraction. When light is incident above the critical angle of total internal reflection (known in the art), all of the incident electromagnetic radiation is reflected and none is transmitted into the low index phase. A thin region of evanescent radiation is established proximal to the interface on the low index side. This radiation field is typically an exponentially decaying field with an attenuation length in the range from about 100 nm to about 200 nm, depending on the angle of incidence and the indices of refraction of the two phases. If the low index phase is a solution containing an analyte, then the evanescent radiation can be used to probe the analyte in the solution with a high degree of surface sensitivity.

In ERC, the carrier of the propagating electromagnetic radiation is a transparent low index film, and the analyte-bearing medium is a high-index metallic opaque film. In this case, most of the radiation is reflected irrespective of the angle of incidence, and non-reflected light is rapidly attenuated according to the skin depth of the metal. Typically, means is provided to convey the analyte within the metal phase. Theses means can take the form of a nanocapillary tube constructed within the metal layer. When sufficiently small, the presence of such a tube will have little effect on the distribution of energy in the two media, but can be amply large enough to convey biomolecules. To be small enough, any defects in the metal film must be small compared with the wavelength of the illumination. This can be achieved because of the large ratio between the wavelength of visible light, and the typical size of biomolecules of interest. While visible light is typically between 400 nm and 750 nm in wavelength, biomolecules of interest are generally in the vicinity of 1-30 nm in diameter. The attenuation of the radiation at the interface can be used to confine illumination to a very small region of the analyte. A small hole in an index matched (to water) film on a high index substrate could provide lateral confinement beyond what is possible with diffraction limited optics in the TIR context. This could give 100 zeptoliter confinement in principle. In this method, a version of total internal reflection confinement is used in which a solid material index-matched to the analyte solution is applied to the substrate surface and then perforated with nanoscale holes. When used in TIR mode, these structures will provide additional confinements above what can be obtained with TIR alone.

Other alternative confinements are index matching solids. As an illustrative example, such optical confinement can be fabricated starting with a high index transparent substrate such as sapphire, spin coat 200 nm of PMMA (polymethyl methacrylate) resist resin. Exposure to electron beam lithography will render isolated spots soluble according to the pattern applied. After development, the device will have nanoscale holes in the PMMA layer and are ready to be used in a TIR setup. Axial confinement is unaffected by the PMMA layer, as it has nearly the same index of refraction as the solution containing the analyte, but the solution is physically prevented from approaching near the surface except where the holes are situated, providing a degree of lateral confinement given by the diameter of the holes.

The subject optical confinements can be provided with an optical system capable of detecting and/or monitoring interactions between reactants at the single-molecule level. Such optical system achieves these functions by first generating and transmitting an incident wavelength to the reactants contained in the confinements, followed by collecting and analyzing the optical signals from the reactants. Such systems typically employ an optical train that directs signals from an array of confinements onto different locations of an array-based detector to simultaneously detect multiple different optical signals from each of multiple different confinements. In particular, the optical trains typically include optical gratings or wedge prisms to simultaneously direct and separate signals having differing spectral characteristics from each confinement in an array to different locations on an array based detector, e.g., a CCD. By separately directing signals from each confinement to different locations on a detector, and additionally separating the component signals from each confinement to separate locations, one can simultaneously monitor multiple confinements, and multiple signals from each confinement.

The optical system applicable for the present invention comprises at least two elements, namely an excitation source and a photon detector. The excitation source generates and transmits incident light used to optically excite the reactants contained in the optical confinement. Depending on the intended application, the source of the incident light can be a laser, a light-emitting diode (LED), a ultra-violet light bulb, and/or a white light source. Where desired, more than one source can be employed simultaneously. The use of multiple sources is particularly desirable in case of detecting more than one fluorescent signal to track the interactions of more than one or one type of molecule simultaneously. A wide variety of photon detectors are available in the art. Representative detectors include but are not limited to optical reader, high-efficiency photon detection system, photodiode (e.g. avalanche photo diodes (APD)), camera, charge couple device (CCD), electron-multiplying charge-coupled device (EMCCD), intensified charge coupled device (ICCD), and confocal microscope equipped with any of the foregoing detectors. Where desired, the subject arrays of optical confinements contain various alignment aides or keys to facilitate a proper spatial placement of the optical confinement and the excitation sources, the photon detectors, or the optical transmission element as described below.

The subject optical system may also include an optical transmission element whose function can be manifold. First, it collects and/or directs the incident wavelength to the optical confinement containing the reactants. Second, it transmits and/or directs the optical signals emitted from the reactants inside the optical confinement to the photon detector. Third, it may select and/or modify the optical properties of the incident wavelengths or the emitted wavelengths from the reactants. Illustrative examples of such element are diffraction gratings, arrayed waveguide gratings (AWG), optic fibers, optical switches, mirrors, lenses (including microlens and nanolens), collimators. Other examples include optical attenuators, polarization filters (e.g., dichroic filter), wavelength filters (low-pass, band-pass, or high-pass), waveplates, and delay lines. In some embodiments, the optical transmission element can be planar waveguides in optical communication with the arrayed optical confinements. For instance, a planar waveguides can be operatively coupled to an array of zero-mode waveguides to directly channel incident wavelengths to the respective cores of the zero-mode waveguides so as to minimize the loss of wave energy. The planar channel can included as a detachable unit located at the base of array substrate, or it can be bonded to the substrate as an integral part of the array.

The optical transmission element suitable for use in the present invention encompasses a variety of optical devices that channel light from one location to another in either an altered or unaltered state. Non-limiting examples of such optical transmission devices include optical fibers, diffraction gratings, arrayed waveguide gratings (AWG), optical switches, mirrors (including dichroic mirrors), lenses (including microlens and nanolens), collimators, filters and prisms, and any other devices that guide the transmission of light through proper refractive indices and geometries.

In a preferred embodiment, the optical confinement of the present invention is operatively coupled to a photon detector. For instance, the arrayed optical confinement is operatively coupled to a respective and separate photon detector. The confinement and the respective detector can be spatially aligned (e.g., 1:1 mapping) to permit an efficient collection of optical signals from the waveguide. A particularly preferred setup comprises an array of zero-mode waveguides, wherein each of the individual waveguides is operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement.

The subject arrays may comprise a single row or a plurality of rows of optical confinements on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is preferred.

The array of optical confinements may be incorporated into a structure that provides for ease of analysis, high throughput, or other advantages, such as in a microtiter plate or multi-well plate and the like. Such setup is also referred to herein as an "array of arrays." For example, the subject arrays can be incorporated into another array such as microtiter plate or multi-well plate wherein each micro well of the plate contains a subject array of optical confinements. Typically, such multi-well plates comprise multiple reaction vessels or wells, e.g., in a 48 well, 96 well, 384 well or 1536 well format. In such cases, the wells are typically disposed on 18 mm, 9 mm, 4.5 mm, or 2.25 mm centers, respectively.

As described above, the subject arrays comprise a plurality of optical confinements. In some embodiments, the arrays have at least about $20\times10^4$ distinct optical confinements, preferably at least about $20\times10^6$ distinct confinements, and more preferably at least about $20\times10^8$ confinements. The density of the spots on the solid surface in certain embodiments is at least above $4\times10^4$ confinements per $mm^2$, and usually at least about $8\times10^4$, at least about $1.2\times10^5$, or at least about $4\times10^6$ confinements per $mm^2$, but does not exceed $4\times10^{12}$ confinements per $mm^2$, and usually does not exceed about $4\times10^{10}$ confinements per $mm^2$. The overall size of the array generally ranges from a few nanometers to a few millimeters in thickness, and from a few millimeters to 50 centimeters in width or length. Preferred arrays have an overall size of about few hundred microns in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements should be placed close to each other relative to the incident wavelength.

Accordingly, in one aspect, the present invention provides an array of zero-mode waveguides comprising at least a first and at least a second zero-mode waveguide, wherein the first zero-mode waveguide is separated from the second zero-mode waveguide by a distance such that upon illumination with an incident wavelength, intensity of diffractive scattering observed from the first zero-mode waveguide at a given angle is less than that if the first zero-mode waveguide were illuminated with the same incident wavelength in the absence of the second zero-mode waveguide. Diffractive scattering can be reduced or significantly eliminated if an array comprises zero-mode waveguides spaced in a regular spaced lattice where the separation of zero-mode waveguides from their nearest neighbors is less than half the wavelength of the incident wavelength. In this regime, the structure behaves as a zero-order grating. Such gratings are incapable of scattering incident light despite having a large number of elements that by themselves would scatter very effectively. This arrangement is highly desirable for illumination approaches such as dark field illumination, where surface scattering would cause excitation radiation to be collected by the objective lens, thus increasing background noise. Useful wavelengths for illumination range from 250 nm up to 8 microns, meaning that an array of zero-mode waveguides with a spacing of less than 4000 nm would still be useful for application in this manner. A spacing of less than 2000 nm is more preferable, while a spacing of less than 1000 nm is even more preferable in this respect. Some configurations with spacing larger than one half of the wavelength can have the same advantage if the illumination is applied asymmetrically, or if the collection cone angle is configured to be less than 90 degrees. In addition to the benefit of reduced diffractive scattering, narrow spacing between the individual confinements decreases the illumination area and thus lowers the power demand.

Arrays having the optical confinements spaced far apart relative to the incident wavelength also have desirable properties. While the angle-dependent scattering raises the background signal that could be disadvantageous for certain applications, it provides a means particularly suited for characterizing the size and shape of the optical confinements. It also readily permits ensemble bulk measurements of molecule interactions, involving especially unlabelled molecules. Arrays suited for such applications generally contain individual confinements separated by more than one wavelength of the incident radiation, usually more than 1.5 times the incident wavelength, but usually does not exceed 150 times the incident wavelength.

Preparation of the Subject Optical Confinements:

The array of the present invention can be manufactured using nanofabrication techniques provided by the present invention, as well as those known in the fields of Integrated Circuit (IC) and Micro-Electro-Mechanical System (MEMS). The fabrication process typically proceeds with selecting an array substrate, followed by using appropriate IC processing methods and/or MEMS micromachining techniques to construct and integrate the optical confinement and other associated components.

Array Substrate:

In some embodiments, the array of optical confinements is present on a rigid substrate. In other embodiments concerning, e.g., porous films with reflective index media, flexible materials can be employed.

In some embodiments, the array of optical confinements is present on a rigid substrate. In other embodiments concerning, e.g., porous films with reflective index media, flexible materials can be employed. In general, a rigid support does not readily bend, i.e., the support is not flexible. Examples of solid materials which are not rigid supports with respect to the present invention include membranes, flexible metal or plastic films, and the like. As such, the rigid substrates of the subject arrays are sufficient to provide physical support and structure to optical confinements present thereon or therein under the assay conditions in which the array is employed, particularly under high throughput handling conditions.

The substrates upon which the subject patterns of arrays are may take a variety of configurations ranging from simple to complex, depending on the intended use of the array. Thus, the substrate could have an overall slide or plate configuration, such as a rectangular or disc configuration, where an overall rectangular configuration, as found in standard microtiter plates and microscope slides, is preferred. Generally, the thickness of the rigid substrates will be at least about 0.01 mm and may be as great as 1 cm or more, but will usually not exceed about 5 cm. Both the length and the width of rigid substrate will vary depending on the size of the array of optical confinements that are to be fabricated thereon or therein.

The substrates of the subject arrays may be fabricated from a variety of materials. The materials from which the substrate is fabricated is preferably transparent to visible and/or UV light. Suitable materials include glass, semiconductors (e.g., silicate, silicon, silicates, silicon nitride, silicon dioxide, quartz, fused silica, and gallium arsenide), plastics, and other organic polymeric materials. In preferred aspects, silica based substrates like glass, quartz and fused silica are used as the underlying transparent substrate material.

The substrate of the subject arrays comprise at least one surface on which a pattern of optical confinements is present, where the surface may be smooth or substantially planar, or have irregularities, such as depressions or elevations. The surface may be modified with one or more different layers of compounds that serve to modulate the properties of the surface in a desirable manner. Modification layers of interest include: inorganic and organic layers such as metals, metal oxides, polymers, small organic molecules, functional moieties such as avidin/biotin and the like. The choice of methods for applying the coating materials will depend on the type of coating materials that is used. In general, coating is carried out by directly applying the materials to the zero-mode waveguide followed by washing the excessive unbound coating material from the surface. Alternatively or additionally, coating materials may be deposited using other conventional techniques, such as chemical vapor deposition (CVD), sputtering, spin coating, in situ synthesis, and the like. Certain coating materials can be cross-linked to the surface via extensive heating, radiation, and/or by chemical reactions. In preferred aspects, suitable coating materials are coupled to substrate surfaces either covalently or through ionic or hydrophobic/hydrophilic interactions. In the case of silica based substrates, for example, silane chemistries are particularly suited for covalently attaching coating materials to surfaces, e.g., coupling groups, specific binding moieties, and the like. Such chemistries are well known to those of ordinary skill in the art and can be practiced without undue experimentation.

Fabrication Process:

Fabrication of the subject array substrates can be performed according to the methods described as follows or other standard techniques of IC-processing and/or MEMS micromachining. The standard techniques known in the art include but are not limited to electron-beam lithography, photolithography, chemical vapor or physical vapor deposition, dry or wet etching, ion implantation, plasma ashing, bonding, and electroplating. Additional fabrication processes are detailed in the U.S. Patent Application Publication No. 20030174992, the content of which is incorporated by reference in its entirety.

Uses of the Subject Optical Confinements and Other Devices of the Present Invention The subject devices including optical confinements and associated optical systems provide an effective means for analyzing molecules and monitoring chemical reactions. The subject device and detection/monitoring methods may be used in a wide variety of circumstances including sequencing individual human genomes as part of preventive medicine, rapid hypothesis testing for genotype-phenotype associations, in vitro and in situ gene-expression profiling at all stages in the development of a multi-cellular organism, determining comprehensive mutation sets for individual clones and profiling in various diseases or disease stages. Other applications include measuring enzyme kinetics, and identifying specific interactions between target molecules and candidate modulators of the target molecule. Further applications involve profiling cell receptor diversity, identifying known and new pathogens, exploring diversity towards agricultural, environmental and therapeutic goals.

In certain embodiments, the subject devices and methods allow high-throughput single-molecule analyses. Single-molecule analyses provide several compelling advantages over conventional approaches to studying biological events. First, the analyses provide information on individual molecules whose properties are hidden in the statistically averaged information that is recorded by ordinary ensemble measurement techniques. In addition, because the analyses can be multiplexed, they are conducive to high-throughput implementation, require smaller amounts of reagent(s), and take advantage of the high bandwidth of optical systems such as modern avalanche photodiodes for extremely rapid data collection. Moreover, because single-molecule counting automatically generates a degree of immunity to illumination and light collection fluctuations, single-molecule analyses can provide greater accuracy in measuring quantities of material than bulk fluorescence or light-scattering techniques. As such, single-molecule analyses greatly improve the efficiency and accuracy in genotyping, gene expression profiling, DNA sequencing, nucleotide polymorphism detection, pathogen detection, and drug screening.

In alternative aspects, instead of using optical confinements to screen away unincorporated nucleotides from observation, one may use other processes to move these nucleotides or nucleotide analogs from the field of observation or detection. Examples of such methods include the use of electrophoretic systems that apply potential gradient across the reaction vessel to drive reagents, e.g., charged nucleotides, away from the field of view, while incorporated nucleotides remain present, preferably attached to a support (either through the template, the nascent strand, or the polymerase template complex). Such electrophoretic systems typically include an electrode layer deposited upon a substrate surface where the polymerase/template complex is immobilized, and a complementary electrode disposed in contact with the reaction solution. A potential is then applied between the two electrodes to drive current flow in a direction such that the unincorporated nucleotides or nucleotide analogs are moved away from the field of view. This movement may be lateral movement to actually move such analogs out of the field of view, or it may be movement orthogonal to the field of view.

Other methods employ fluidic systems coupled to the reaction vessel or a portion thereof to flow unincorporated nucleotides out of the field of view. For example, such systems may include microfluidic channels that flow reagents away from and back into contact with the polymerase/template complex. Alternatively, such systems may provide a constant level of flowing reagents passing by the complex. When a given analog is incorporated by the complex, it's retention at the complex will make signal from it's now immobilized label, distinguishable from the transient signals of analogs that are flowing past in the background.

General Methodology of Nucleic Acid Sequencing:

The subject devices including various forms of optical confinements and the associated optical systems are particularly suited for multiplexed nucleic acid sequencing, and especially single-molecule sequencing. Accordingly, the present invention provides a method of sequencing a target nucleic acid. The method general involves (a) providing an optical confinement of the present invention; (b) mixing in the confinement the target nucleic acid molecules, primers complementary to the target nucleic acid molecules, polymerization enzymes, and more than one type of nucleotides or nucleotide analogs that are extension terminators to be incorporated into nascent nucleotide strand; (c) subjecting the mixture to a polymerization reaction under conditions suitable for formation of the nascent nucleotide strand by template-directed extension of primer; (d) illuminating the optical confinement with an incident light beam to cleave the blocking group on the terminator and/or to identify the nucleotide that is incorporated into the nascent nucleotide strand of at least two consecutive bases.

In some embodiments, temporal order of base additions during the polymerization reaction is identified on a single molecule of nucleic acid. Such identifying step takes place while the template-directed extension of primer or polymerization is taking place within the optical confinement. In a preferred embodiment, single-molecule sequencing is performed in a homogenous assay that does not require transfer, separation or washing away any reactant or by-product (e.g. fluorophore cleaved from a nucleotide, or the blocking group) after each base addition event. In some aspect of the homogenous assay, single-molecule sequencing is performed without adding reactants to the mixture prior to reading the next base sequence.

The subject method provides numerous advantages over other sequencing methods. First, stepwise removal of by-product after each base addition event is not necessary. The method allows the use of target nucleic acid molecules taken directly from a biological sample, minimizing the need for cloning, subcloning, or amplification of the target nucleic acids before sequencing can take place.

Exemplary Experimental Setup:

In practicing the subject sequencing method, a reaction mixture comprising the target nucleic acids, primers complementary to the target nucleic acids, polymerization enzymes, and more than one type of nucleotides or nucleotide analogs, is applied to the optical confinements. Where desired, each optical confinement receives only one target nucleic acid molecule that is to be sequenced. This can be achieved by diluting a minute amount of target nucleic acids in a large volume of solution containing the rest of the reactants required for the sequencing process. Alternatively, a non-cylindrical waveguide, wherein the opening of the waveguide core is narrower in lateral dimension than the base, can be used to restrict the entry of multiple target nucleic acids.

Immobilization of the Target Nucleic Acid or the Polymerase to an Optical Confinement:

The target nucleic acid can be immobilized to the inner surface of the optical confinement by a number of ways. For example, the target nucleic acid can be immobilized by attaching (1) a primer or (2) a single-stranded or (3) double-stranded or partially double-stranded target nucleic acid molecule. Thereafter, either (1) the target nucleic acid molecule is hybridized to the attached oligonucleotide primer, (2) an oligonucleotide primer is hybridized to the immobilized target nucleic acid molecule, to form a primed target nucleic acid molecule complex, or (3) a recognition site for the polymerase is created on the double stranded or partially double stranded target nucleic acid (e.g., through interaction with accessory proteins, such as a primase). A nucleic acid polymerizing enzyme on the primed target nucleic acid molecule complex is provided in a position suitable to move along the target nucleic acid molecule and extend the oligonucleotide primer at an active site.

In another embodiment, the polymerization enzyme is first attached to a surface of the subject optical confinement in a position suitable for the target nucleic acid molecule complex to move relative to the polymerization enzyme.

One skilled in the art will appreciate that there are many ways of immobilizing nucleic acids and enzymes on a solid surface, whether covalently or noncovalently, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either the nucleic acids or the polymerases to a solid support include streptavidin or avidin/biotin, carbamate, ester, amide, thiolester, (N)-functionalized thiourea, functionalized maleimide, amino, disulfide, amide, and hydrazone, among others. Antibody that specifically binds to the target nucleic acid or polymerase can also be employed as the binding moieties.

In some embodiments, the target nucleic acids are linear DNA molecules. In other embodiments, the target nucleic acids are non-linear DNA molecules including without limitation circular DNA molecules.

The binding moieties and either the polymerase or nucleic acids they immobilize can be applied to the support by conventional chemical techniques which are well known in the art. In general, these procedures can involve standard chemical surface modifications of the support, incubation of the support at different temperatures in different media, and possible subsequent steps of washing and incubation of the support surface with the respective molecules.

Reaction Mixture: Labeled Nucleotides, Polymerases, and Primers

The various types of nucleotides or nucleotide analogs utilized in accordance with the subject sequencing methods (including single-molecule sequencing method) are conjugated with detectable labels so that a photon detector can detect and distinguish their presence within the subject optical confinements. Preferred labels are luminescent labels, and especially fluorescent or chromogenic labels.

A variety of functional groups used as detectable labels in nucleotides has been developed in the art. Table 1 lists numerous examples of such functional groups. Additional examples are described in U.S. Pat. No. 6,399,335, which is incorporated herein by reference.

TABLE 1

| Exemplary detectable label functional groups | |
|---|---|
| 4-aminophenol | 6-aminonaphthol |
| 4-nitrophenol | 6-nitronaphthol |
| 4-methylphenol | 6-chloronaphthol |
| 4-methoxyphenol | 6-bromonaphthol |
| 4-chlorophenol | 6-iodonaphthol |
| 4-bromophenol | 4,4'-dihydroxybiphenyl |
| 4-iodophenol | 8-hydroxyquinoline |
| 4-nitronaphthol | 3-hydroxypyridine |
| 4-aminonaphthol | umbelliferone |
| 4-methylnaphthol | Resorufin |
| 4-methoxynaphthol | 8-hydroxypyrene |
| 4-chloronaphthol | 9-hydroxyanthracene |
| 4-bromonaphthol | 6-nitro9-hydroxyanthracene |
| 4-iodonaphthol | 3-hydroxyflavone |
| 6-methylnaphthol | Fluorescein |
| 6-methoxynaphthol | 3-hydroxybenzoflavone |

Using these and other functional groups, a vast diversity of fluorophores suitable for the present sequencing method have been generated. They include but are not limited to 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcoumarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonc acid; 4,4'-diisothiocyanatostilbene-2,2'-disulfonic acid; 5-[dimethylamino]

naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron.RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Additional fluorophores applicable for the subject sequencing method are disclosed in U.S. Pat. No. 5,866,366 and WO 01/16375, both of which are incorporated herein by reference.

The labels can be attached to a variety of positions on the phosphate backbone, on the base, on the ribose unit, or a combination thereof. In some embodiments, labels are those that do not substantially impede the continuous addition of nucleotides in a sequencing reaction. Such labels include those linked to the alpha phosphates, the beta phosphates, the gamma phosphates or selected positions on the base units of the nucleotides.

Nucleotides comprising a labeled gamma phosphate are particularly preferred because no additional means is required to remove the labels in the sequencing procedure. During the synthesis of DNA, the bond cleavage in the nucleotide occurs between the alpha and the beta phosphate, causing the beta and gamma phosphates to be released from the active site after polymerization, and the formed pyrophosphate subsequently diffuses away from the nascent strand. Therefore, labels attached to the gamma phosphate are separated from the nascent strand once the nucleotides are being incorporated. Table 1 lists numerous examples of nucleotides that are labeled at the gamma phosphate position. Many other gamma-phosphate-linked nucleotides have been developed and are detailed in U.S. Pat. No. 6,399,335, which is incorporated herein by reference in its entirety.

TABLE 2

Adenosine-5'-(γ-4-nitrophenyl)triphosphate
Guanosine-5'-(γ-4-nitrophenyl)triphosphate
Cytosine-5'-(γ-4-nitrophenyl)triphosphate
Thymidine-5'-(γ-4-nitrophenyl)triphosphate
Uracil-5'-(γ-4-nitrophenyl)triphosphate
3'-azido-3'-deoxythymidine-5'-(γ-4-nitrophenyl)triphosphate
3'-azido-2',3'-dideoxythymidine-5'-(γ-4-nitrophenyl)triphosphate
2',3'-didehydro-2',3'-dideoxythymidine-5'-(γ-4-nitrophenyl)triphosphate
Adenosine-5'-(γ-4-aminophenyl)triphosphate
Adenosine-5'-(γ-4-methylphenyl)triphosphate
Adenosine-5'-(γ-4-methoxyphenyl)triphosphate
Adenosine-5'-(γ-4-chlorophenyl)triphosphate
Adenosine-5'-(γ-4-bromophenyl)triphosphate TABLE 2-continued Adenosine-5'-(γ-4-iodophenyl)triphosphate
Adenosine-5'-(γ-4-nitronaphthyl)triphosphate
Adenosine-5'-(γ-4-aminonaphthyl)triphosphate
Adenosine-5'-(γ-4-methylnaphthyl)triphosphate
Adenosine-5'-(γ-4-methoxynaphthyl)triphosphate
Adenosine-5'-(γ-4-chloronaphthyl)triphosphate
Adenosine-5'-(γ-4-bromonaphthyl)triphosphate
Adenosine-5'-(γ-4-iodonaphthyl)triphosphate
Adenosine-5'-(γ-6-methylnaphthyl)triphosphate
Adenosine-5'-(γ-6-methoxynaphthyl)triphosphate
Adenosine-5'-(γ-6-aminonaphthyl)triphosphate
Adenosine-5'-(γ-6-nitronaphthyl)triphosphate
Adenosine-5'-(γ-6-chloronaphthyl)triphosphate
Adenosine-5'-(γ-6-bromonaphthyl)triphosphate
Adenosine-5'-(γ-6-iodonaphthyl)triphosphate
Adenosine-5'-(γ-4'-hydroxybiphenyl)triphosphate
Adenosine-5'-(γ-8-quinolyl)triphosphate
Adenosine-5'-(γ-3-pyridyl)triphosphate
Adenosine-5'-(γ-umbelliferone)triphosphate
Adenosine-5'-(γ-resorufin)triphosphate
Adenosine-5'-(γ-pyrene)triphosphate
Adenosine-5'-(γ-anthracene)triphosphate
Adenosine-5'-(γ-6-nitroanthracene)triphosphate
Adenosine-5'-(γ-flavonyl)triphosphate
Adenosine-5'-(γ-fluorescein)triphosphate
Adenosine-5'-(γ-benzoflavone)triphosphate
Adenosine-5'-(γ-(4-nitrophenyl)-γ'-(4-aminophenyl)triphosphate
Adenosine-5'-(γ-(4-nitrophenyl)-γ'-(4-nitronaphthyl)triphosphate The nucleotides or nucleotide analogs used in the subject methods are typically reversible extension terminators incorporating blocking moieties which can be deblocked or cleaved when needed, thus conferring selective control to either proceed to the next step of nucleotide incorporation or to delay incorporation in order to first detect the nucleotide just being incorporated into the nascent strand. The selective removal of these blocking moieties allows revealing an active ribose site for incorporation subsequent nucleotide analogs, revealing a detectable signal, and/or revealing a hybridizable base.

The blocking moieties can serve the aforementioned function by way of enzymatic, thermal, catalytic, and/or photon dependent cleavage mechanisms. For example, enzymatically cleavable groups may be provided in a position on an analog that will prevent incorporation of subsequent nucleotide analogs once the analog has been incorporated. In some cases, these groups may be provided at the 3' position of the ribose, however in many cases, they will be proximal to the 3' position so that they sterically inhibit a subsequent incorporation event until they have been removed. Such groups include carbohydrate groups that may be selectively cleaved from the incorporated nucleotide analogs, proteolytically digestible groups, and the like.

Figure 4:
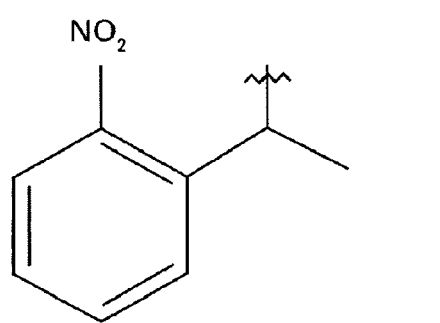
FIG. 4 depicts exemplary photocleavable blocking groups and the applicable wavelengths applied to cleave the blocking groups.
Figure 4:
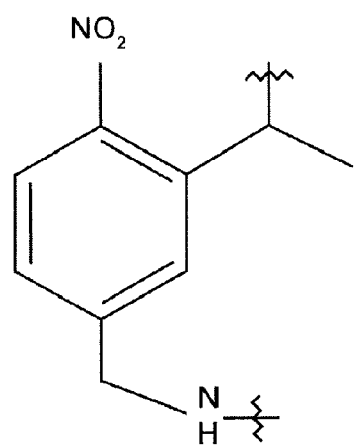

A preferred class of reversible extension terminators incorporate photocleavable blocking groups. A wide variety of different photolabile blocking groups can be employed in the present invention. For example, o-nitrobenzyl blocking groups, such as those described in U.S. Pat. No. 5,773,308, incorporated herein by reference in its entirety for all purposes. Similarly, nitroveratryl, 1-pyrenylmethyl, 6-nitroveratryloxycarbonyl, dimethyldimethoxybenzyloxycarbonyl, 2-nitrobenzyloxycarbonyl, 5-bromo-7-nitroindolinyl, O-hydroxy-alpha-methyl-cinnamoyl, methyl, 6-nitroveratryloxycarbonyl, methyl-6-nitropiperonyloxycarbonyl, and 2-oxymethylene anthraquinone, dimethoxybenzyloxy carbonyl, 5-bromo-7-nitroindolinyl, o-hydroxy-alpha-methyl cinnamoyl, 2-oxymethylene anthriquinone, and mixtures thereof, as described in U.S. Pat. Nos. 5,412,087 and 5,143,854, have been employed in the synthetic production of nucleic acids for use in biomolecular arrays, and the like. Non-limiting examples of such moieties are depicted in FIG. 4, as well as those described in the references cited herein, all of which are incorporated by reference for all purposes.

In some embodiments, the blocking group as a whole comprises both a blocking function and a linker to the detectable label. In other embodiments, the blocking group and the detectable label are located on different units of a nucleotide analog (i.e., ribose, base, terminal phosphates, or analogs thereof, including but not limited to sulfur derivatives).

Figure 5:
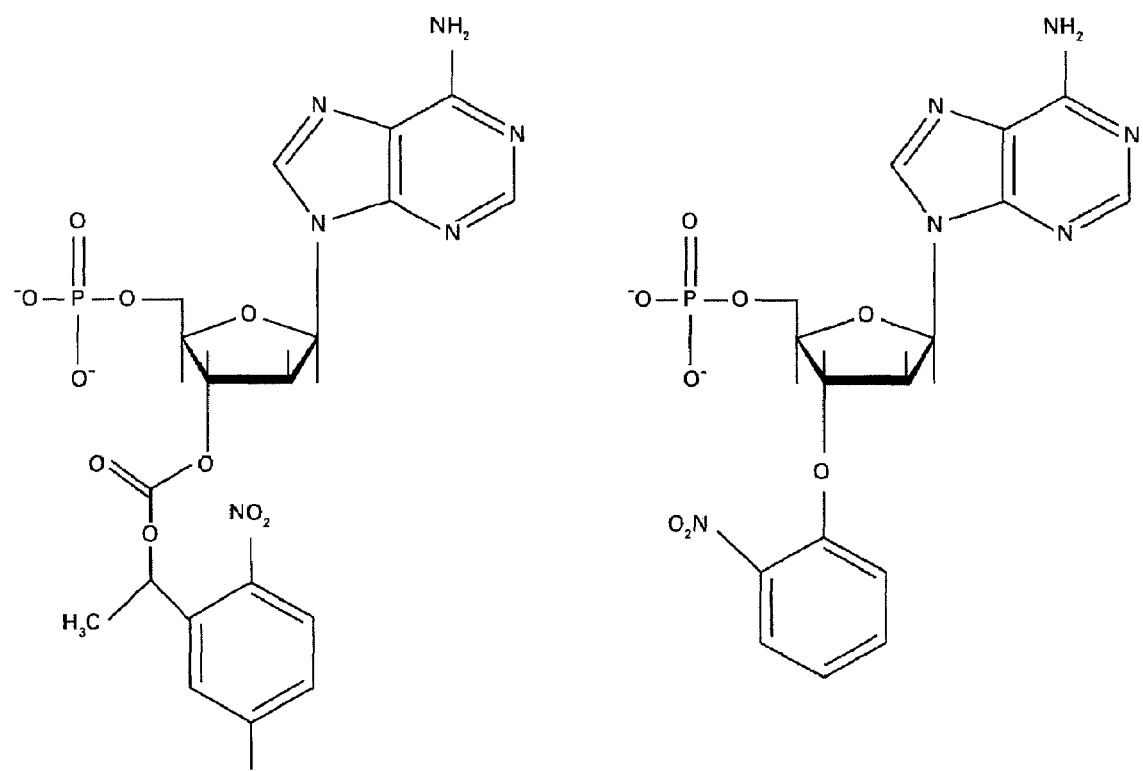
FIG. 5 depicts exemplary reversible extension terminators in which the photocleavable blocking group is attached to the ribose unit of the nucleotide at the 3' position.
Figure 6:
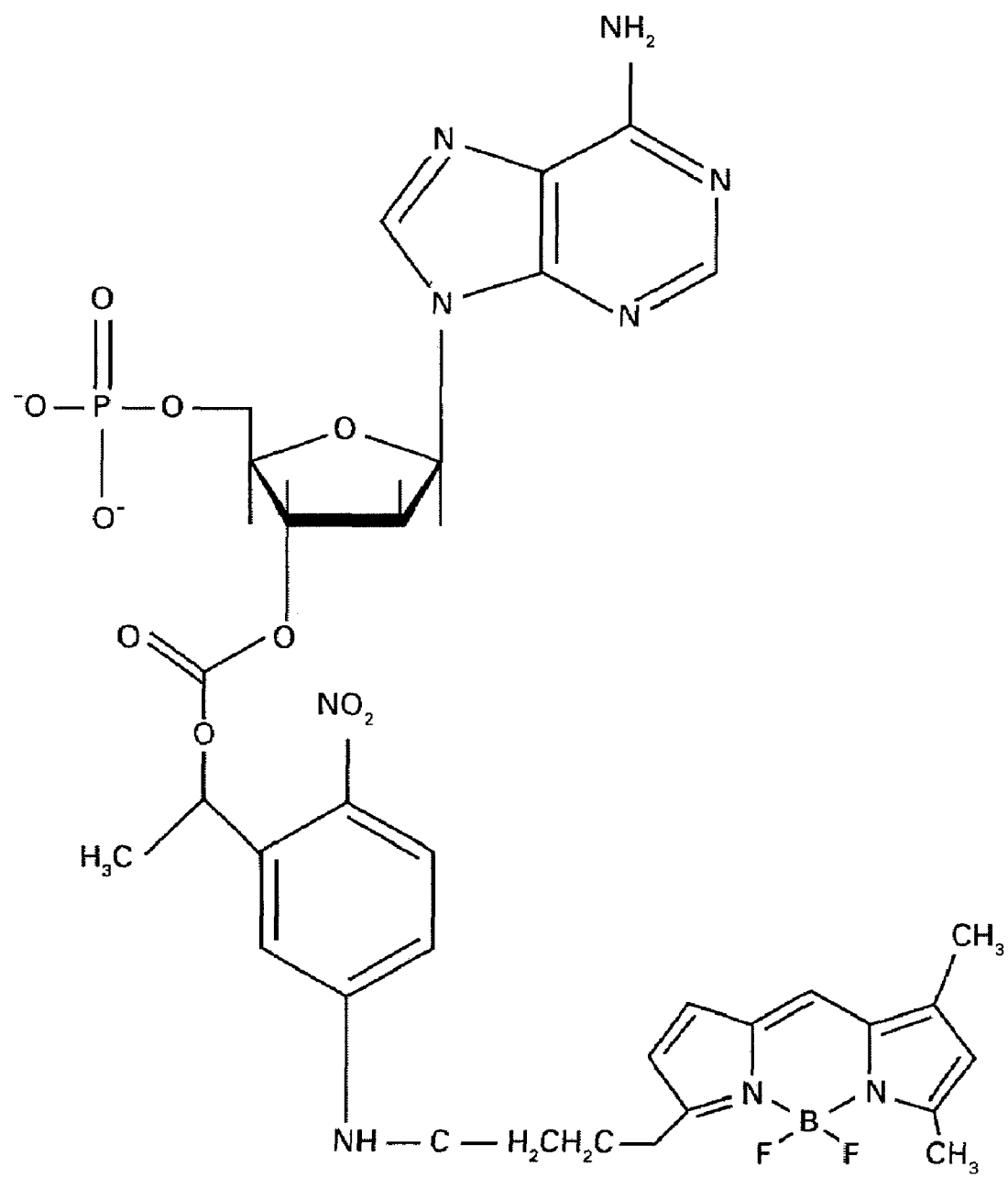
FIG. 6 depicts an exemplary reversible extension terminator in which the photocleavable blocking group at the 3' position of ribose is conjugated to a detectable label (e.g. fluorescent label).

In some embodiments, the reversible extension terminator that comprises a ribose blocked with the reversible blocking group at the 3' end can be employed to conduct single-molecule sequencing. The blocking group is generally removed before the next nucleotide addition event can take place. Preferred 3'-ribose labels comprise photo-removable functional groups that can be deprotected upon exposure to a light beam at suitable wavelength. In conjunction with the present invention, such blocking groups are coupled to the 3' position of a nucleotide being added to a growing strand. The presence of the 3' blocking group then causes a cessation of polymerase induced synthesis. Following detection, photoexposure of the synthesizing strand removes the protecting group thus leaving it open for addition of the subsequent nucleotide analog. Exemplary reversible extension terminators of this type are depicted in FIG. 5, in which photoremoval of the blocking groups can be accomplished upon irradiation at i.e., about 340 nm. In some embodiments, the blocking group on the reversible extension terminator may further comprise a linker. Such a linker may connect a detectable label, quencher, and/or other functional group. An exemplary reversible extension terminator is depicted in FIG. 6. In other embodiments, the reversible extension terminator can comprise a blocking group at the 2' or 4' position of the ribose.

Figure 7:
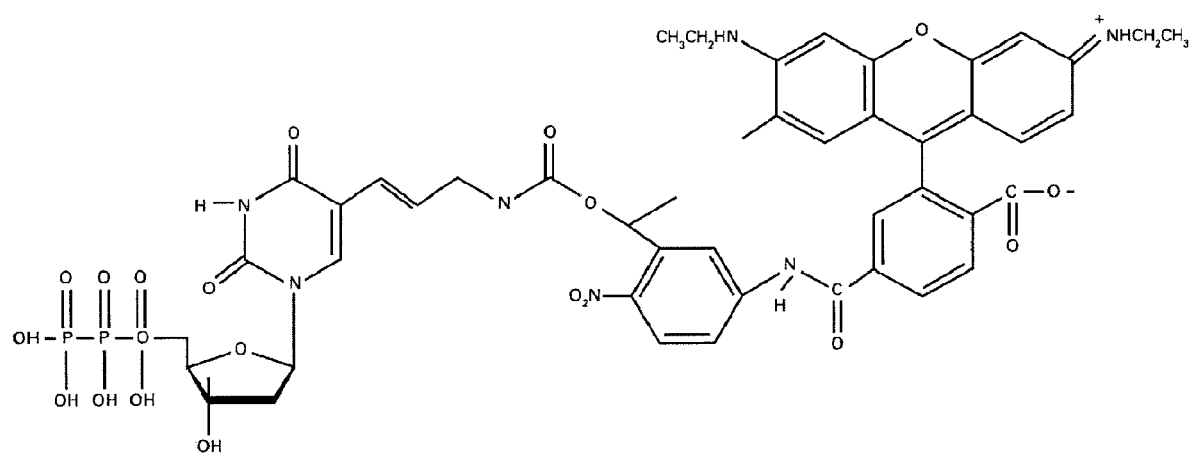
FIG. 7 depicts an exemplary reversible extension terminator in which the photocleavable blocking group is attached to the base unit of the nucleotide and to a detectable label (e.g. fluorescent label).
Figure 8:
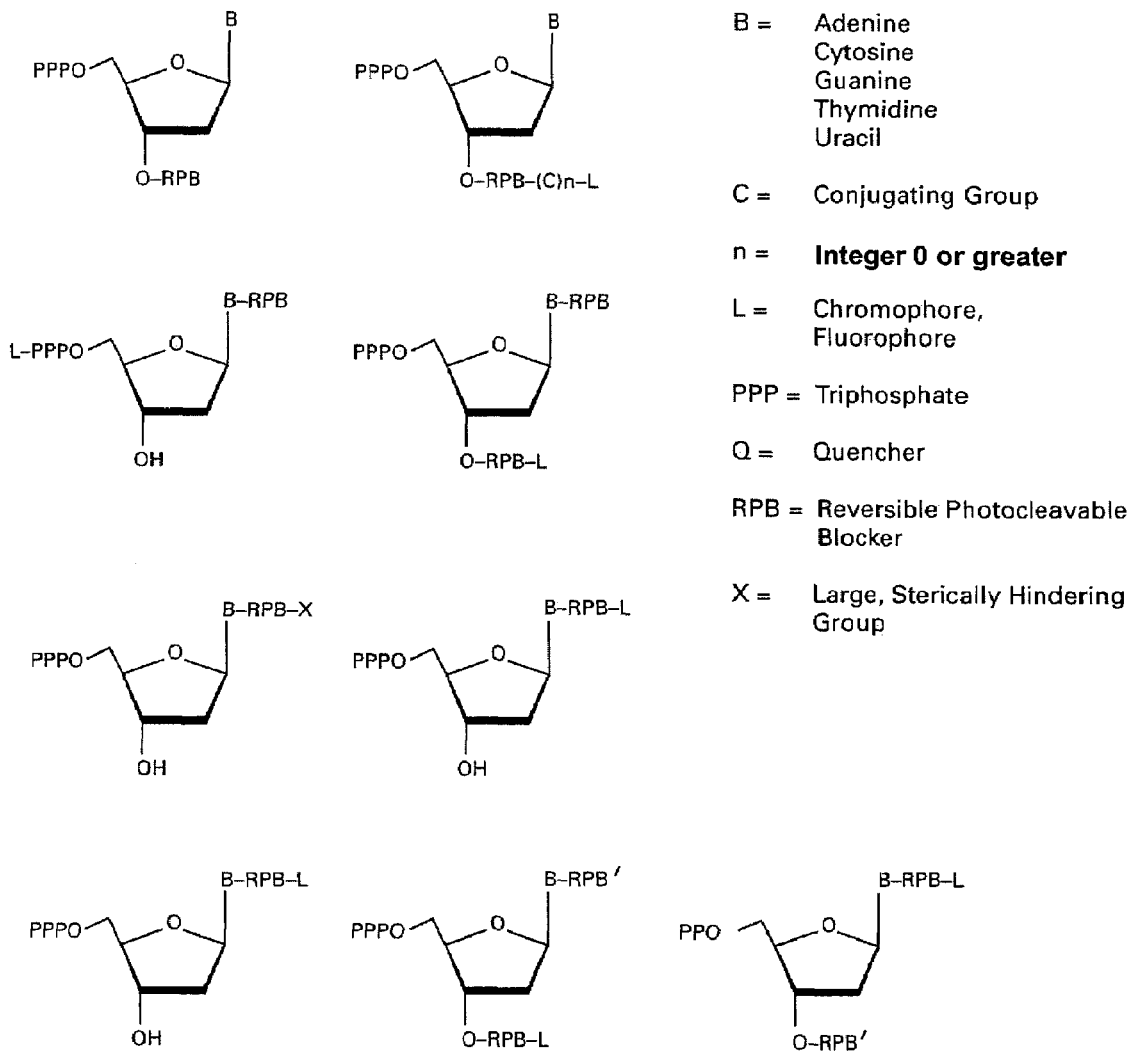
FIG. 8 depicts schematic representations of a variety of reversible extension terminators.

In other embodiments, the blocking group and the detectable label are located at different portions of a nucleotide analog. For example, the reversible blocking group is linked to or conjugated to the base (adenine, thymine, cytosine, guanine, or uracil) of the terminator, whereas the detectable label is attached to the ribose or the terminal phosphate of the ribose. An exemplary reversible extension terminator of such type is depicted in FIG. 8. In some embodiments of this aspect of the invention, the reversible blocking group is linked or conjugated to any of the following, including C2, C4, C5, N3 and C6 of cytosine, uracil, and thymine. The blocking group can be conjugated via the carbonyl functionality at C2 of cytosine, uracil, or thymine, or via the methyl functionality at C5 of thymine, or any combinations of the above. In other examples, the reversible group is linked or conjugated to any of the following, including C2, C6, C8, N3 and N7 of adenine and guanine. The blocking group can be conjugated via the carbonyl functionality at C6 in guanine, or via the amino functionality at C6 in adenine, or via N3 or N7 in adenine or guanine, or via the amino functionality at C6 in guanine, or any combinations of the above. In other embodiments, the blocking group can further comprise a detectable label. A non-limiting example is depicted in FIG. 7. In some other embodiments, the detectable label for identifying the particular type of nucleotide analog incorporated into a nascent strand can function as a reversible blocking group by way of steric hindrance. In other embodiments, the reversible blocking group may further comprise another sterically hindering group sufficiently large enough to prevent incorporation of the subsequent nucleotide analog until the removal of the blocking group. An example of this type of reversible extension terminator is depicted in FIG. 8. In another embodiment of the invention, two blocking groups, each being photocleavable at distinct wavelengths, are attached to different portions of the nucleotide analog (e.g., the first blocking group, 1-(2-nitrophenyl)ethyl (deprotection wavelength 300-350 nm), being located on the ribose and the second, 5-bromo-7-nitroindolinyl (deprotection wavelength at 420 nm) located on the base), permitting differential deblocking. An exemplary reversible extension terminator of such type is depicted in FIG. 8.

Figure 2:
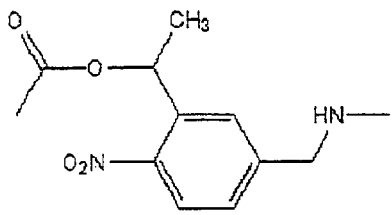
FIGS. 2a.)-d.) depicts exemplary photocleavable blockers and the applicable wavelength applied to cleave the blocking group.
Figure 2:
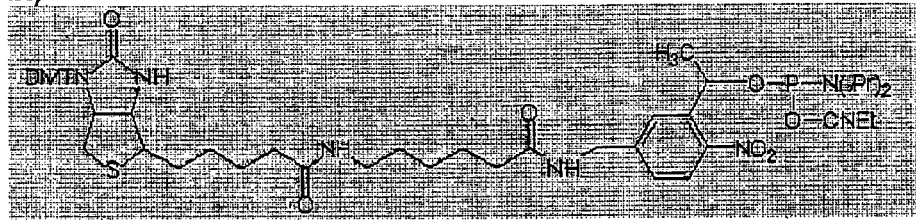
Figure 2:
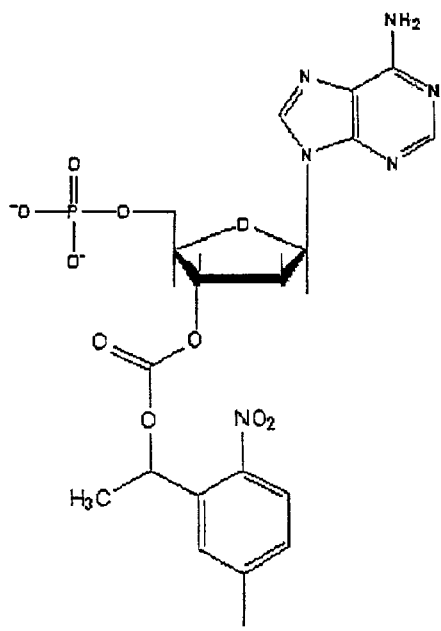
Figure 2:
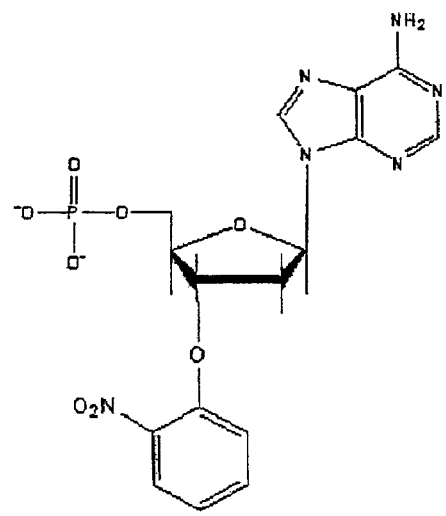
Figure 3:
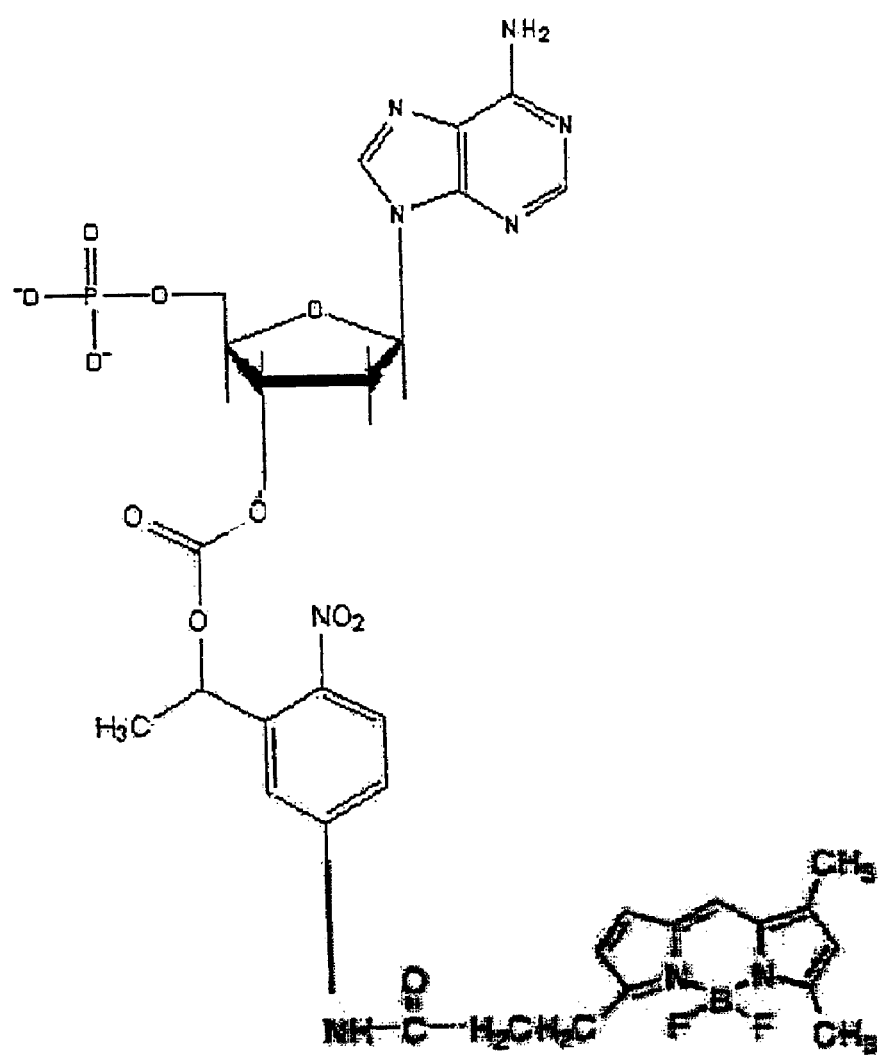
FIG. 3 depicts an exemplary reversible extension terminator in which the photocleavable blocker is conjugated to a detectable label (e.g. fluorescent label).

Other suitable examples of reversible blocking groups and especially photocleavable blocking groups include but are not limited to those molecules depicted in FIGS. 2 and 3, and those described in the references in the appended reference list, all which are incorporated herein by reference.

The wavelength used to cleave the photocleavable blocking groups will depend on the choice of the blocking group. The wavelength may range from about 320 nm to about 800 nm. In some embodiments, the wavelength for cleaving the blocking group is about the same as the wavelength used to detect the label. In other embodiments, the wavelength for cleaving the blocking group is different from the wavelength used to detect the label.

As described above, removal of the labels after they have been detected and identified in accordance with the sequencing procedure of the present invention may be beneficial for detecting the next nucleotide that is to be incorporated. Suitable means for removing the labels after the nucleotide has been incorporated into the nascent strand includes photobleaching of the fluorescent labels or photochemical cleavage of the nucleotide and the fluorophore, e.g., cleavage of a chemical bond in the linker, or by any procedure suitable for removing labels without damaging the sequencing reaction complex. The rate of removing the fluorescent label of already incorporated nucleotides can be adjusted by the laser power, which in turn prevents accumulation of signal on the nucleic acid strand, thereby maximizing the signal to noise ratio for nucleotide identification. For this scheme, the objective of the present invention is to detect all of the photons emitted from each label and then photobleach or photochemically cleave before or soon after the next few nucleotides are incorporated in order to maintain adequate signal to noise values for subsequent identification steps.

Figure 9:
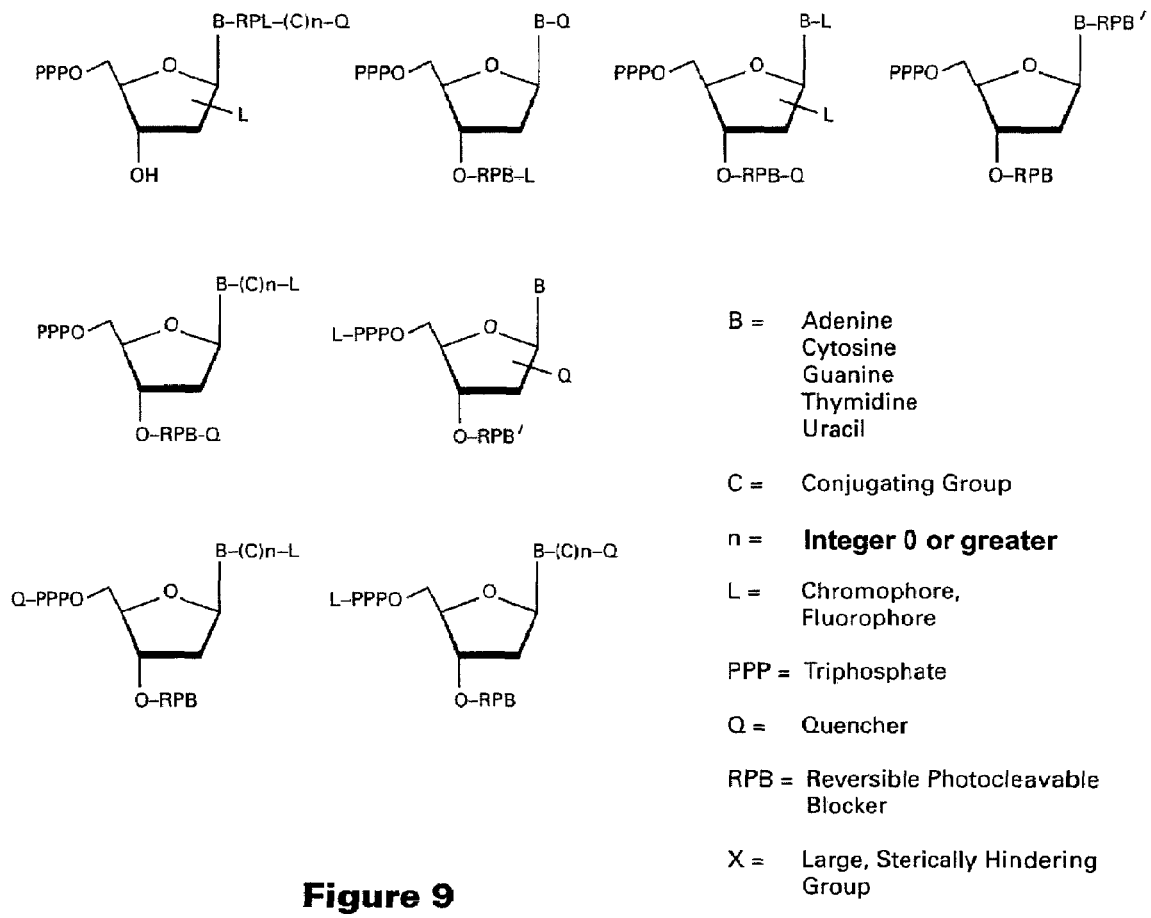
FIG. 9 depicts schematic representations of a variety of reversible extension terminators which incorporate quenchers.

Another type of suitable nucleotide for the subject sequencing method comprises a fluorophore attached to the gamma phosphate and a fluorescence quencher attached to either the base or the sugar. Upon incorporation of the nucleotide into the nascent strand, the released pyrophosphate becomes fluorescent as the attached fluorophore is unquenched. By determining the order of the fluorescent pyrophosphate that is released upon incorporating a complementary nucleotide during the polymerization event, one can deduce the base sequence of the target nucleic acid. This type of nucleotide is disclosed in U.S. application No. 2003019470, which is incorporated herein by reference. In some embodiments of reversible extension terminators, the blocking group further comprises a fluorescence quencher, which is usually attached to a different portion of the nucleotide analog than where the detectable label is attached. In one example of this type of reversible extension terminators, the quencher is attached via the reversible blocker to the base, while the detectable label is attached to the ribose. Alternatively, the quencher is attached via the removable blocker to the 3'position of the ribose, while the detectable label is attached to the base. In a third alternative, the detectable label is attached to the base, the quencher is attached to the terminal phosphate, and the 3' position of the ribose is blocked with the photocleavable blocking group. In another embodiment, the detectable label is attached to the phosphate, the quencher to the base and the photocleavable blocking group is attached to the 3' position of the ribose. Examples of reversible extension terminators of this type are depicted in FIG. 9.

In some applications of this class of nucleotide, the fluorophore and quencher function by an electron transfer mechanism (FET). In this aspect, an excited fluorophore (the donor) transfers its excited state energy to a light absorbing molecule (the acceptor) which does not release the energy radioactively. The optical properties of a wide range of donors and acceptors suitable for such application are known in the art (see, e.g. Haugland, Handbook of Fluorescent Probes and Research Chemicals (Molecular Probes, Eugene, 1992). Representative donors and acceptors capable of fluorescence energy transfer include, but are not limited to, 4-acetamido-4'-isothiocyanatostilbene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)$_4$-methylcoumarin; diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amin-ofluorescein (DTAF), 2',7'-dimethoxy4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.™. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N, N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

Preferred fluorophore-quencher pairs include, but are not limited to, xanthene dyes, including fluoresceins, and rhodamine dyes. Many of the preferred dyes contain modified substituents on their phenyl moieties which can be used as the site for bonding to the gamma phosphate or the base of a nucleotide. Where desired, quenchers capable of quenching a wide range of wavelengths of fluorescence can be used. Representative examples of such quenchers include 4-(4'-dimethylaminophenylaz-o)-benzoic acid (DABCYL), dinitrophenyl (DNP) and trinitrophenyl (TNP). Additional suitable fluorophore-quencher pairs are disclosed in U.S. application No. 2003019470 (supra).

The polymerization enzyme utilized in accordance with the present invention can be any nucleic acid polymerases that are capable of catalyzing template-directed polymerization with reasonable synthesis fidelity. The polymerases can be DNA polymerases or RNA polymerases, a thermostable polymerase or a thermally degradable polymerase. Non-limiting examples for suitable thermostable polymerases include polymerases isolated from *Thermus aquaticus, Thermus thermophilus, Pyrococcus woesei, Pyrococcus furiosus, Thermococcus litoralis*, and *Thermotoga maritima*. Useful thermodegradable polymersases include *E. coli* DNA polymerase, the Klenow fragment of *E. coli* DNA polymerase, T4 DNA polymerase, T7 DNA polymerase.

Additional examples of polymerization enzymes that can be used to determine the sequence of nucleic acid molecules include *E. coli* T7, T3, SP6 RNA polymerases and AMV, M-MLV and HIV reverse transcriptases. The polymerase can be bound to the primed target nucleic acid sequence at a primed single-stranded nucleic acid, an origin of replication, a nick or gap in a double-stranded nucleic acid, a secondary structure in a single-stranded nucleic acid, a binding site created by an accessory protein, or a primed single-stranded nucleic acid.

In a preferred embodiment, sequencing is carried out with polymerases exhibiting a high degree of processivity, i.e., the ability to synthesize long stretches of nucleic acid by maintaining a stable nucleic acid/enzyme complex. A processive polymerase can typically synthesize a nascent strand over about 10 kilo bases. With the aid of accessory enzymes (e.g., helicases/primases), some processive polymerases can synthesize even over 50 kilobases. For instance, it has been shown that T7 DNA polymerase complexed with helicase/primase can synthesize several 100 kilobases of nucleotides while maintaining a stable complex with the target nucleic acid.

In another preferred embodiment, sequencing is performed with polymerases exhibiting strand-displacement activity. Such polymerases include but are not limited to phi29 polymerases and mutants thereof.

Using the subject method, sequencing can be carried out at the speed of at least 1 base per second, preferably at least 10 bases per second, more preferably at least 100 bases per second.

Reaction Conditions:

The sequencing procedure can also be accomplished using less than 4 labels employed. With 3 labels, the sequence can be deduced from sequencing a nucleic acid strand (1) if the 4th base can be detected as a constant dark time delay between the signals of the other labels, or (2) unequivocally by sequencing both nucleic acid strands, because in this case one obtains a positive fluorescence signal from each base pair. Another possible scheme that utilizes two labels is to have one base labelled with one fluorophore and the other three bases with another fluorophore. In this case, the other 3 bases do not give a sequence, but merely a number of bases that occur between the particular base being identified by the other fluorophore. By cycling this identifying fluorophore through the different bases in different sequencing reactions, the entire sequence can be deduced from sequential sequencing runs. Extending this scheme of utilizing two labels only, it is even possible to obtain the full sequence by employing only two labelled bases per sequencing run. As was pointed out by Sauer et al., "Detection and Identification of Single Dye Labelled Mononucleotide Molecules Released From an Optical Fiber in a Microcapillary: First Steps Towards a New Single Molecule DNA Sequencing Technique," Phys. Chem. Chem. Phys. 1:2471-77 (1999), which is hereby incorporated by reference, the sequence can be determined with 2 labels alone if one carries out multiple sequencing reactions with the possible combinations of the two labels. Therefore, in carrying out the process of the present invention, it is desirable to label long stretches of nucleic acid with at least 2 different labels.

Detection:

The subject sequencing method requires the imaging of individual molecules confined in an optical confinement. The polymerase and/or the nucleotides are typically labeled with fluorophores that emit a distinguishable optical signal when a particular type of nucleotide is incorporated into the nascent strand. The sequence of the distinguishable signals is detected as the nucleotides are sequentially added to the nascent strand within the optical confinement. In a preferred embodiment, such detection is performed without the need for transfer, separation or washing away of any reactant or by-product (e.g. fluorophore cleaved from a nucleotide) after each nucleotide addition event. In one aspect of this preferred embodiment, sequence detection is performed without adding reactants to the mixture prior to reading the next base sequence.

Imaging individual molecules confined in the subject optical confinements is performed with the aid of an optical system. Such system typically comprises at least two elements, namely an excitation source and a photon detector.

In a preferred embodiment, the excitation source is a laser, preferably a polarized laser. The choice of laser light will depend on the fluorophores attached to the different type of nucleotides and/or the polymerases. For most of the fluorescent compounds, the required excitation light is within the range of about 300 nm to about 800 nm. For proteinaceous fluorophores such as green-fluorescent protein and mutants thereof, the excitation wavelength may range from about 488 nm to about 404 nm. Those skilled in the art will know or will be able to ascertain the appropriate excitation wavelength to excite a given fluorophore by routine experimentation.

Another consideration in selecting an excitation source is the choice between one-photon and multiphoton excitation of fluorescence. Multiphoton excitation coupled with detection, also known as multiphoton micropscopy ("MPM"), provides enhanced sensitivity and spatial resolution. MPM is a form of laser-scanning microscopy that uses localized nonlinear excitation to excite fluorescence within a thin raster-scanned plane. In MPM, as in conventional laser-scanning confocal microscopy, a laser is focused and raster-scanned across the sample. The image consists of a matrix of fluorescence intensity measurements made by digitizing the detector signal as the laser sweeps back and forth across the sample. Two-photon excitation probabilities are extremely small, and focusing increases the local intensity at the focal point. Although two-photon excited fluorescence is usually the primary signal source in MPM, three-photon or more excited fluorescence and second or third-harmonic generation can also be used for imaging. See, e.g., a review of multiphoton micropscopy in Webb et al. *Nature Biotechnology* (2003) 21: (11)1251-1409. A preferred MPM setup comprises MPM laser scanning microscopes and second-harmonic imaging, equipped with femtosecond mode-locked titanium sapphire lasers operating at wavelengths from 700 to 1,000 nm. Such setup can capture more than about 100 photons per pixel in most of the conventional imaginary multiphoton microscope.

The sequence of the distinguishable signals can also be detected by other optical systems comprising elements such as optical readers, high-efficiency photon detection systems, photo multiplier tubes, chemically sensitive FET's (ChemFETs), including nano-tube or nanowire based FET's, P/N diodes, photodiodes (e.g. avalanche photo diodes (APD)), camera, charge couple devices (CCD), electron-multiplying charge-coupled devices (EMCCD), intensified charge coupled devices (ICCD), and confocal microscopes equipped with any of the foregoing detection or imaging systems.

A preferred combination comprises wide field CCD and intensified video imaging microscopes with digital image processing capability, as well as Fluorescence Photobleaching Recovery (FPR) and Fluorescence Correlation Spectroscopy (FCS) with confocal multiphoton capability and continuous data acquisition and control. Such set up may further comprise modular instrument for quasi-elastic light scattering, laser DIC interferometry, correlation spectroscopy instrumentation, components of optical force microscopy, and Time Correlated Single Photon Counting (TCSPC). Additional applicable detection devices include scanning microscopes (e.g., scanning confocal microscopy, scanning two photon microscope).

These optical systems may also comprise optical transmission elements such as diffraction gratings, arrayed waveguide gratings (AWG), optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements.

These and other optical components known in the art can be combined and assembled in a variety of ways to effect detection of the distinguishable signals emitted from the sequencing reaction. Preferred setup allows parallel data collection using arrays having a large number of optical confinements, where simultaneous and independent sequencing of nucleic acids takes place. In one aspect, the preferred setup can collect and process signals from more than $10^5$ optical confinements, preferably more than $10^6$, and even more preferably more than $10^7$ optical confinements. In another aspect, the preferred setup can monitor in real time the simultaneous and independent sequencing of nucleic acids at a speed of about 1 base per second, preferably at a speed of about 10 bases per second, more preferably at a speed of about 100 bases per second and even more preferably at 1,000 bases per second.

EXAMPLE

The following provides an illustrative process of nucleic acid sequencing in an optical confinement using reversible extension terminator(s). The parameters described herein are meant to be illustrative and not intended to be limiting in any manner.

For purpose of illustration, the confinement employed for sequencing is an array of zero mode waveguide structures on a transparent surface, and the reversible terminator is a 3' modified nucleotide triphosphate analog having one of the carboxylate linked photocleavable linkers with a fluorophore attached (see, e.g. FIG. 3). For this molecule and a category of molecules like it, the photocleavage of the blocking group results in a chain of reactions that both removes the fluorophore from the molecule and creates a 3' OH moiety on the ribose sugar to allow further polymerization. Each channel is one zero mode waveguide structure element from the array of structures.

In this embodiment, the light collection system is a high numerical aperture lens, and the molecule discrimination system is a color separation system with a sensitive single-photon counting detector such as an avalanche photodiode with a single photon counting module. The array of confinements is mounted on a stage which is used to align the array to the illumination and detection systems. The DNA sample to be sequenced, the DNA polymerase, the nucleotides and other reaction mixture components are introduced into the system, either before or after mounting and alignment of the system. Illuminating radiation is directed to the channel of interest, e.g., one or more waveguides on the array of confinements, and light is collected back from that channel through the use of an optical scanning system, several types of which are known in the art. (e.g. confocal scanning microscopes available from, e.g., BioRad, galvo scanner microscopes, etc.). The illumination and detection are scanned from one channel to the next, dwelling at each for a period of time that is either predetermined or determined at the time of measurement using information from the detector. In one version of this embodiment, the illumination and detection zone is scanned at constant speed across the array, and the effective dwell time is determined by the speed of passage and the width of the observation region.

When an incorporation event occurs on a particular channel, the next time the observation region is positioned over the zero mode waveguide structure of that channel, the illumination radiation excites fluorescence in the incorporated labeled nucleotide analog. This fluorescence emission is collected by the detection system and converted into signal which can then be analyzed to allow the determination of identity of the corresponding base in the nucleotide sequence. If the photoreactive component is activated at the same wavelength as the excitation of the fluorophore, then the illuminating radiation is continued for a period of time to cleave the fluorophore from the nucleotide and allow further polymerization. If the cleavage wavelength is different from the fluorescence excitation wavelength, then illumination at the cleavage wavelength is applied at a time later than the fluorescence excitation wavelength, either by a predetermined amount, or using information from the molecule discrimination system to trigger application of the cleavage illumination.

Information collected in association with particular channel is collated and stored together. The process is iterated for each channel of interest in the system to effect a scan of the array of confinements. Then, the scan is repeated a plurality of times until the desired sequence information has been determined.

The present invention is further understood with reference to a number of scientific journal articles, the full disclosures of which are incorporated herein by reference:

A Pentaerythritol-Based Molecular Scaffold for Solid-Phase Combinatorial Chemistry Farcy, N.; De Muynck, H.; Madder, A.; Hosten, N.; De Clercq, P. J.; Org. Lett.; (Communication); 2001; 3(26); 4299-4301.

Synthesis and Characterization of a Photocleavable Cross-Linker and Its Application on Tunable Surface Modification and Protein Photodelivery Yan, F.; Chen, L.; Tang, Q.; Wang, R.; Bioconjugate Chem.; (Article); 2004; 15(5); 1030-1036.

Combinatorial Chemistry. Synthesis and Application Edited by Stephen R. Wilson and Anthony W. Czarnik. John Wiley & Sons. 1997.

A New Photocleavable Linker in Solid-Phase Chemistry for Ether Cleavage Glatthar, R.; Giese, B.; Org. Lett.; (Communication); 2000; 2(15); 2315-2317.

Synthesis of a Small Molecule Combinatorial Library Encoded with Molecular Tags John J. Baldwin, Jonathan J. Burbaum, Ian Henderson, Michael H. J. Ohlmeyer; J. Am. Chem. Soc.; 1995; 117(20); 5588-5589.

Core-Shell-Type Resins for Solid-Phase Peptide Synthesis: Comparison with Gel-Type Resins in Solid-Phase Photolytic Cleavage Reaction Kim, H.; Cho, J. K.; Chung, W.-J.; Lee, Y.-S.; Org. Lett.; (Communication); 2004; 6(19); 3273-3276.

Sequentially Photocleavable Protecting Groups in Solid-Phase Synthesis Kessler, M.; Glatthar, R.; Giese, B.; Bochet, C. G.; Org. Lett.; (Communication); 2003; 5(8); 1179-1181.

Simultaneous Triggering of Protein Activity and Fluorescence Pellois, J.-P.; Hahn, M. E.; Muir, T. W.; J. Am. Chem. Soc.; (Communication); 2004; 126(23); 7170-7171.

General Inverse Solid-Phase Synthesis Method for C-Terminally Modified Peptide Mimetics Sasubilli, R.; Gutheil, W. G.; J. Comb. Chem.; (Article); 2004; 6(6); 911-915.

Practical Synthesis of a Dithiane-Protected 3',5'-Dialkoxybenzoin Photolabile Safety-Catch Linker for Solid-Phase Organic Synthesis Cano, M.; Ladlow, M.; Balasubramanian, S.; J. Org. Chem.; (Article); 2002; 67(1); 129-135.

Studies on the Chemical Stability and Functional Group Compatibility of the Benzoin Photolabile Safety-Catch Linker Using an Analytical Construct Cano, M.; Ladlow, M.; Balasubramanian, S.; J. Comb. Chem.; (Article); 2002; 4(1); 44-48.

Phototriggering of Caged Fluorescent Oligodeoxynucleotides Tang, X. J.; Dmochowski, I. J.; Org. Lett.; (Communication); 2005; 7(2); 279-282.

Protecting Groups in Solid-Phase Organic Synthesis Orain, D.; Ellard, J.; Bradley, M.; J. Comb. Chem.; (Review); 2002; 4(1); 1-16.

Photolytic Mass Laddering for Fast Characterization of Oligomers on Single Resin Beads Burgess, K.; Martinez, C. I.; Russell, D. H.; Shin, H.; Zhang, A. J.; J. Org. Chem.; (Communication); 1997; 62(17); 5662-5663.

Tools for Combinatorial Chemistry: Real-Time Single-Bead Infrared Analysis of a Resin-Bound Photocleavage Reaction Pivonka, D. E.; Simpson, T. R.; Anal. Chem.; (Technical Note); 1997; 69(18); 3851-3853.

High-Resolution $^1$H NMR in Solid-Phase Organic Synthesis William L. Fitch, George Detre, Christopher P. Holmes, James N. Shoolery, Paul A. Keifer; J. Org. Chem.; 1994; 59(26); 7955-7956.

Polymer-Supported Oligosaccharides via n-Pentenyl Glycosides: Methodology for a Carbohydrate Library $\perp^1$ Rodebaugh, R.; Joshi, S.; Fraser-Reid, B.; Geysen, H. M.; J. Org. Chem.; (Communication); 1997; 62(17); 5660-5661.

A New Supported Reagent for the Photochemical Generation of Radicals in Solution De Luca, L.; Giacomelli, G.; Porcu, G.; Taddei, M.; Org. Lett.; (Communication); 2001; 3(6); 855-857.

Stereoselective Synthesis of over Two Million Compounds Having Structural Features Both Reminiscent of Natural Products and Compatible with Miniaturized Cell-Based Assays Tan, D. S.; Foley, M. A.; Shair, M. D.; Schreiber, S. L.; J. Am. Chem. Soc.; (Communication); 1998; 120(33); 8565-8566.

Multiple-Component Condensation Strategies for Combinatorial Library Synthesis Armstrong, R. W.; Combs, A. P.; Tempest, P. A.; Brown, S. D.; Keating, T. A.; Acc. Chem. Res.; (Article); 1996; 29(3); 123-131.

De Novo Asymmetric Bio- and Chemocatalytic Synthesis of Saccharides—Stereoselective Formal O-Glycoside Bond Formation Using Palladium Catalysis Comely, A. C.; Eelkema, R.; Minnaard, A. J.; Feringa, B. L.; J. Am. Chem. Soc.; (Communication); 2003; 125(29); 8714-8715.

Identification of Novel Macrocyclic Peptidase Substrates via On-Bead Enzymatic Cyclization Hansen, K. K.; Hansen, H. C.; Clark, R. C.; Bartlett, P. A.; J. Org. Chem.; (Article); 2003; 68(22); 8459-8464.

The Dithianyl Group as a Synthon in Porphyrin Chemistry: Condensation Reactions and Preparation of Formylporphyrins under Basic Conditions Senge, M. O.; Hatscher, S. S.; Wiehe, A.; Dahms, K.; Kelling, A.; J. Am. Chem. Soc.; (Communication); 2004; 126(42); 13634-13635.

Photoactivation of toxin conjugates Victor S. Goldmacher, Peter D. Senter, John M. Lambert, Walter A. Blattler; Bioconjugate Chem.; 1992; 3(2); 104-107.

Solid-Phase Synthesis of β-Sultams Gordeev, M. F.; Gordon, E. M.; Patel, D. V.; J. Org. Chem.; (Article); 1997; 62(23); 8177-8181.

Preparation and Photoactivation of Caged Fluorophores and Caged Proteins Using a New Class of Heterobifunctional, Photocleavable Cross-Linking Reagents Ottl, J.; Gabriel, D.; Marriott, G.; Bioconjugate Chem.; (Article); 1998; 9(2); 143-151.

Steroids and Combinatorial Chemistry Maltais, R.; Tremblay, M. R.; Ciobanu, L. C.; Poirier, D.; J. Comb. Chem.; (Review); 2004; 6(4); 443-456.

Model Studies for New o-Nitrobenzyl Photolabile Linkers: Substituent Effects on the Rates of Photochemical Cleavage Holmes, C. P.; J. Org. Chem.; (Article); 1997; 62(8); 2370-2380.

Evaluation of a Two-Stage Screening Procedure in the Combinatorial Search for Serine Protease-Like Activity Madder, A.; Li, L.; De Muynck, H.; Farcy, N.; Van Haver, D.; Fant, F.; Vanhoenacker, G.; Sandra, P.; Davis, A. P.; De Clercq, P. J.; J. Comb. Chem.; (Article); 2002; 4(6); 552-562.

Stable-Isotope Dimethyl Labeling for Quantitative Proteomics Hsu, J.-L.; Huang, S.-Y.; Chow, N.-H.; Chen, S.-H.; Anal. Chem.; (Article); 2003; 75(24); 6843-6852.

Synthesis and Evaluation of Macrocyclic Transition State Analogue Inhibitors for α-Chymotrypsin Hansen, K. K.; Grosch, B.; Greiveldinger-Poenaru, S.; Bartlett, P. A.; J. Org. Chem.; (Article); 2003; 68(22); 8465-8470.

Studies on a Dithiane-Protected Benzoin Photolabile Safety Catch Linker for Solid-Phase Synthesis Lee, H. B.; Balasubramanian, S.; J. Org. Chem.; (Article); 1999; 64(10); 3454-3460.

Reversible Biotinylation Phosphoramidite for 5'-End-Labeling, Phosphorylation, and Affinity Purification of Synthetic Oligonucleotides Fang, S.; Bergstrom, D. E.; Bioconjugate Chem.; (Article); 2003; 14(1); 80-85.

Agonists of the Follicle Stimulating Hormone Receptor from an Encoded Thiazolidinone Library Maclean, D.; Holden, F.; Davis, A. M.; Scheuerman, R. A.; Yanofsky, S.; Holmes, C. P.; Fitch, W. L.; Tsutsui, K.; Barrett, R. W.; Gallop, M. A.; J. Comb. Chem.; (Article); 2004; 6(2); 196-206.

Concerted Intercalation and Minor Groove Recognition of DNA by a Homodimeric Thiazole Orange Dye Bunkenborg, J.; Gadjev, N. I.; Deligeorgiev, T.; Jacobsen, J. P.; Bioconjugate Chem.; (Article); 2000; 11(6); 861-867.

Direct Mass Spectrometric Monitoring of Solid Phase Organic Syntheses Gerdes, J. M.; Waldmann, H.; J. Comb. Chem.; (Article); 2003; 5(6); 814-820.

Libraries of Multifunctional RNA Conjugates for the Selection of New RNA Catalysts Hausch, F.; Jaschke, A.; Bioconjugate Chem.; (Article); 1997; 8(6); 885-890.

Photochemically and photoenzymatically cleavable DNA Sourena Nadji, Cheng I. Wang, John Stephen Taylor; J. Am. Chem. Soc.; 1992; 114(24); 9266-9269.

Automated Affinity Capture-Release of Biotin-Containing Conjugates Using a Lab-on-Valve Apparatus Coupled to UV/Visible and Electrospray Ionization Mass Spectrometry Ogata, Y.; Scampavia, L.; Ruzicka, J.; Scott, C. R.; Gelb, M. H.; Turecek, F.; Anal. Chem.; (Article); 2002; 74(18); 4702-4708.

Competitive Photochemical Reactivity in a Self-Assembled Monolayer on a Colloidal Gold Cluster Hu, J.; Zhang, J.; Liu, F.; Kittredge, K.; Whitesell, J. K.; Fox, M. A.; J. Am. Chem. Soc.; (Article); 2001; 123(7); 1464-1470.

Linker-Mediated Modulation of the Chemiluminescent Signal from $N^{10}$-(3-Sulfopropyl)-N-sulfonylacridinium-9-carboxamide Tracers Adamczyk, M.; Chen, Y.-Y.; Fishpaugh, J. R.; Mattingly, P. G.; Pan, Y.; Shreder, K.; Yu, Z.; Bioconjugate Chem.; (Article); 2000; 11(5); 714-724.

Quantification in Proteomics through Stable Isotope Coding: A Review Julka, S.; Regnier, F.; J. Proteome Res.; (Review); 2004; 3(3); 350-363.

Solid-Phase Oligosaccharide Synthesis and Combinatorial Carbohydrate Libraries Seeberger, P. H.; Haase, W.-C.; Chem. Rev.; (Review); 2000; 100(12); 4349-4394.

Photolytic cleavage of DNA by nitrobenzamido ligands linked to 9-aminoacridines gives DNA polymerase substrates in a wavelength-dependent reaction Peter E. Nielsen, Michael Egholm, Troels Koch, Joern B. Christensen, Ole Buchardt; Bioconjugate Chem.; 1991; 2(1); 57-66.

The Kinetics of Helix Unfolding of an Azobenzene Cross-Linked Peptide Probed by Nanosecond Time-Resolved Optical Rotatory Dispersion Chen, E.; Kumita, J. R.; Woolley, G. A.; Kliger, D. S.; J. Am. Chem. Soc.; (Article); 2003; 125(41); 12443-12449.

Absolute Quantification of Specific Proteins in Complex Mixtures Using Visible Isotope-Coded Affinity Tags Lu, Y.; Bottari, P.; Turecek, F.; Aebersold, R.; Gelb, M. H.; Anal. Chem.; (Article); 2004; 76(14); 4104-4111.

Patterning Multiple Aligned Self-Assembled Monolayers Using Light Ryan, D.; Parviz, B. A.; Linder, V.; Semetey, V.; Sia, S. K.; Su, J.; Mrksich, M.; Whitesides, G. M.; Langmuir; (Article); 2004; 20(21); 9080-9088.

Solid-Phase Synthesis for the Identification of High-Affinity Bivalent Lectin Ligands Debenham, S. D.; Snyder, P. W.; Toone, E. J.; J. Org. Chem.; (Article); 2003; 68(15); 5805-5811.

Design and Synthesis of Visible Isotope-Coded Affinity Tags for the Absolute Quantification of Specific Proteins in Complex Mixtures Bottari, P.; Aebersold, R.; Turecek, F.; Gelb, M. H.; Bioconjugate Chem.; (Article); 2004; 15(2); 380-388.

Proteomics in 2002: A Year of Technical Development and Wide-Ranging Applications Figeys, D.; Anal. Chem.; (Review); 2003; 75(12); 2891-2905.

Synthesis and Preliminary Evaluation of a Library of Polycyclic Small Molecules for Use in Chemical Genetic Assays Tan, D. S.; Foley, M. A.; Stockwell, B. R.; Shair, M. D.; Schreiber, S. L.; J. Am. Chem. Soc.; (Article); 1999; 121(39); 9073-9087.

Linkers and Cleavage Strategies in Solid-Phase Organic Synthesis and Combinatorial Chemistry Guillier, F.; Orain, D.; Bradley, M.; Chem. Rev.; (Review); 2000; 100(6); 2091-2158.

Characterization of TAT-Mediated Transport of Detachable Kinase Substrates† Soughayer, J. S.; Wang, Y.; Li, H.; Cheung, S.-H.; Rossi, F. M.; Stanbridge, E. J.; Sims, C. E.; Allbritton, N. L.; Biochemistry; (Article); 2004; 43(26); 8528-8540.

Abstracts, Division of Biological Chemistry, 226th National Meeting of the American Chemical Society, Sep. 7-11, 2003 Biochemistry; (Review); 2003; 42(28); 8594-8652.

Discovery of 4-Substituted Pyrrolidone Butanamides as New Agents with Significant Antiepileptic Activity Kenda, B. M.; Matagne, A. C.; Talaga, P. E.; Pasau, P. M.; Differding, E.; Lallemand, B. I.; Frycia, A. M.; Moureau, F. G.; Klitgaard, H. V.; Gillard, M. R.; Fuks, B.; Michel, P.; J. Med. Chem.; (Article); 2004; 47(3); 530-549.

The "One-Bead-One-Compound" Combinatorial Library Method Lam, K. S.; Lebl, M.; Krchnak, V.; Chem. Rev.; (Review); 1997; 97(2); 411-448.

Synthesis and Applications of Small Molecule Libraries Thompson, L. A.; Ellman, J. A.; Chem. Rev.; (Review); 1996; 96(1); 555-600.

Four-color DNA sequencing by synthesis on a chip using ph fluorescent nucleotides Seo, T. S.; Bai X.; Kim, D. H.; Meng, Q.; Ruparel, H.; Li, Z.,; Turro, N. J.; Ju, J. Proc. Natl. Acad. Sci. U.S.A., 2005, Apr. 26; 102(17); 5926-5931.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A method for identifying a base in a template nucleic acid, comprising:
    (a) providing an optical confinement;
    (b) providing a reaction mixture within the optical confinement, the reaction mixture comprising the template nucleic acid, a polymerase enzyme, and at least a first nucleotide analog, wherein the first nucleotide analog comprises a photolabile blocking group that terminates chain extension of a nascent nucleic acid strand when the first nucleotide analog is incorporated into the nascent nucleic acid strand; and
    (c) identifying the base in the template nucleic acid strand by detecting the incorporated nucleotide analog.

2. The method of claim 1, further comprising:
    removing the photolabile blocking group; and
    repeating the providing and identifying steps of (b) and (c) with at least a second nucleotide analog that comprises a photolabile blocking group that terminates chain extension of a nascent nucleic acid strand when the second nucleotide analog is incorporated into the nascent nucleic acid strand.

3. The method of claim 1, wherein the first nucleotide analog is present in the reaction mixture at a concentration greater than about 1 micromolar.

4. The method of claim 1, wherein the first nucleotide analog is present in the reaction mixture at a concentrations greater than about 50 micromolar.

5. The method of claim 1, wherein the first nucleotide analog is present in the reaction mixture at a concentration greater than about 100 micromolar.

6. The method of claim 1, wherein the first nucleotide analog comprises a fluorescent label.

7. The method of claim 1, wherein the removable blocking group comprises the fluorescent label.

8. The method of claim 1 wherein the removable blocking group is coupled to a 3' position of the nucleotide analog.

9. The method of claim 2, wherein the first and second nucleotide analogs are concurrently present in the reaction mixture.

10. The method of claim 9, wherein the first and second nucleotide analogs each comprise a fluorescent label.

11. The method of claim 1, wherein the reaction mixture comprises at least four different types of nucleotide analogs.

12. The method of claim 11, wherein each of the four different nucleotide analogs comprises a different fluorescent label.

13. The method of claim 1, wherein the optical confinement provides an effective observation volume that is less than 100 zeptoliters.

14. The method of claim 1, wherein the optical confinement provides an observation volume that is less than 50 zeptoliters.

15. The method of claim 1, wherein the optical confinement provides an observation volume that is less than 10 zeptoliters.

16. The method of claim 1, wherein the optical confinement comprises a zero mode waveguide.

17. The method of claim 1, further comprising providing a plurality of optical confinements, providing a reaction mixture within each of the plurality of optical confinements, each reaction mixture comprising the template nucleic acid, a polymerase enzyme, and at least a first nucleotide analog, wherein the first nucleotide analog comprises a photolabile blocking group that terminates chain extension of a nascent nucleic acid strand when the first nucleotide analog is incorporated into the nascent nucleic acid strand.

18. The method of claim 17, wherein the identifying step comprises detecting incorporation of the at least first nucleotide analog into a nascent nucleic acid strand in one or more of the plurality of optical confinements.

19. The method of claim 17, wherein the identifying step comprises detecting incorporation in a subset of the plurality of optical confinements at a time.

20. The method of claim 17, wherein the identifying step comprises detecting incorporation in one optical confinement at a time.

21. The method of claim 17, wherein the identifying step comprises monitoring a plurality of optical confinements at a time.

22. A system, comprising:
    an optical confinement;
    a reaction mixture disposed within the optical confinement, the reaction mixture comprising a template nucleic acid, a polymerase enzyme, and at least a first nucleotide analog, wherein the first nucleotide analog comprises a photolabile blocking group that terminates chain extension of a nascent nucleic acid strand when the first nucleotide analog is incorporated into the nascent nucleic acid strand.

23. The system of claim 22, comprising a detector positioned proximal to the optical confinement to detect incorporation of the first nucleotide analog into the nascent nucleic acid strand.

24. The system of claim 23, wherein the first nucleotide analog comprises a fluorescent label, and the detector comprises a fluorescence detector.

25. The system of claim 22, wherein the optical confinement comprises a zero mode waveguide disposed upon or within a substrate.

26. The system of claim 22, further comprising an array of zero mode waveguides disposed upon or within a substrate.

27. A method for identifying a base in a template nucleic acid, comprising:
(a) providing a reaction mixture comprising the template nucleic acid, a polymerase enzyme, and at least a first nucleotide analog, wherein the first nucleotide analog comprises a removable blocking group that terminates chain extension of a nascent nucleic acid strand when the first nucleotide analog is incorporated into the nascent nucleic acid strand;
(b) identifying the base in the template nucleic acid strand by detecting the incorporated nucleotide analog;
(c) removing the removable blocking group from the incorporated nucleotide analog; and
(d) repeating at least the identifying and removing steps with at least a second nucleotide analog without depleting at least one reagent from the reaction mixture of (a).

28. The method of claim 27, wherein the reaction mixture is provided in an optical confinement.

29. The method of claim 1, wherein a single complex of the template nucleic acid and the polymerase enzyme is contained in said optical confinement.

30. The method of claim 28, wherein a single complex of the template nucleic acid and the polymerase enzyme is contained in said optical confinement.

31. The system of claim 22, wherein a single complex of the template nucleic acid and the polymerase enzyme is contained in said optical confinement.

32. The method of claim 27, wherein the first nucleotide analog is present in the reaction mixture at a concentration greater than about 1 micromolar.

33. The method of claim 27, wherein the first nucleotide analog is present in the reaction mixture at a concentrations greater than about 50 micromolar.

34. The method of claim 27, wherein the first nucleotide analog is present in the reaction mixture at a concentration greater than about 100 micromolar.

35. The method of claim 27, wherein the first nucleotide analog comprises a fluorescent label.

36. The method of claim 27, wherein the removable blocking group comprises the fluorescent label.

37. The method of claim 27, wherein the removable blocking group is coupled to a 3' position of the nucleotide analog.

38. The method of claim 27, wherein the first and second nucleotide analogs are concurrently present in the reaction mixture.

39. The method of claim 27, wherein the first and second nucleotide analogs each comprise a fluorescent label.

40. The method of claim 27, wherein the reaction mixture comprises at least four different types of nucleotide analogs.

41. The method of claim 40, wherein each of the four different nucleotide analogs comprises a different fluorescent label.

42. The method of claim 28, wherein the optical confinement provides an effective observation volume that is less than 100 zeptoliters.

43. The method of claim 28, wherein the optical confinement provides an observation volume that is less than 50 zeptoliters.

44. The method of claim 28, wherein the optical confinement provides an observation volume that is less than 10 zeptoliters.

45. The method of claim 28, wherein the optical confinement comprises a zero mode waveguide.

46. The method of claim 28, further comprising providing a plurality of optical confinements, providing a reaction mixture within each of the plurality of optical confinements, each reaction mixture comprising the template nucleic acid, a polymerase enzyme, and at least a first nucleotide analog, wherein the first nucleotide analog comprises a removable blocking group that terminates chain extension of a nascent nucleic acid strand when the first nucleotide analog is incorporated into the nascent nucleic acid strand.

47. The method of claim 46, wherein the identifying step comprises detecting incorporation of the at least first nucleotide analog into a nascent nucleic acid strand in one or more of the plurality of optical confinements.

48. The method of claim 46, wherein the identifying step comprises detecting incorporation in a subset of the plurality of optical confinements at a time.

49. The method of claim 46, wherein the identifying step comprises detecting incorporation in one optical confinement at a time.

50. The method of claim 46, wherein the identifying step comprises monitoring a plurality of optical confinements at a time.

51. The method of claim 2 or 27, wherein the step of removing the removable blocking group is effected by illuminating the optical confinement with an incident light beam to cleave the blocking group.

* * * * *